United States Patent
Matsumoto et al.

(10) Patent No.: US 7,833,170 B2
(45) Date of Patent: Nov. 16, 2010

(54) NEEDLE-INSERTION DEVICE

(75) Inventors: Daisuke Matsumoto, Kyoto (JP); Hidefumi Komuro, Kyoto (JP); Tetsuya Sakata, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 152 days.

(21) Appl. No.: 10/538,813

(22) PCT Filed: Dec. 11, 2003

(86) PCT No.: PCT/JP03/15913

§ 371 (c)(1),
(2), (4) Date: Jun. 13, 2005

(87) PCT Pub. No.: WO2004/054445

PCT Pub. Date: Jul. 1, 2004

(65) Prior Publication Data

US 2006/0129065 A1 Jun. 15, 2006

(30) Foreign Application Priority Data

Dec. 13, 2002 (JP) .............................. 2002-362483
Dec. 17, 2002 (JP) .............................. 2002-365162

(51) Int. Cl.
*A61B 5/00* (2006.01)
*B65D 81/00* (2006.01)
*A61B 17/32* (2006.01)

(52) U.S. Cl. ...................... 600/583; 600/584; 606/181; 606/182

(58) Field of Classification Search ................ 600/573, 600/583, 584, 575–579; 606/167, 181–183
See application file for complete search history.

(56) References Cited

U.S. PATENT DOCUMENTS

| | | | | |
|---|---|---|---|---|
| 4,548,205 A | * | 10/1985 | Armeniades et al. | ........ 600/561 |
| 4,600,403 A | * | 7/1986 | Wagner | ...................... 604/115 |
| 5,201,560 A | * | 4/1993 | Golden | ...................... 294/64.2 |
| 5,320,607 A | * | 6/1994 | Ishibashi | .................... 604/115 |
| 5,891,053 A | | 4/1999 | Sesekura | |
| 6,071,251 A | | 6/2000 | Cunningham et al. | |
| 6,083,236 A | * | 7/2000 | Feingold | ..................... 606/166 |
| 6,612,111 B1 | * | 9/2003 | Hodges et al. | ............. 600/584 |
| 2003/0109808 A1 | * | 6/2003 | Takinami et al. | ............ 600/584 |

FOREIGN PATENT DOCUMENTS

| | | |
|---|---|---|
| EP | 0 555 554 | 8/1993 |
| JP | 7-51251 | 2/1995 |
| JP | 7-255706 | 10/1995 |

(Continued)

*Primary Examiner*—Max Hindenburg
*Assistant Examiner*—John Pani
(74) *Attorney, Agent, or Firm*—Hamre, Schumann, Mueller & Larson, P.C.

(57) ABSTRACT

This invention relates to a lancing apparatus (A1) used for inserting an insertion element (21) into a human skin (Sk) for sampling a body fluid. The lancing apparatus (A1) includes a housing (1) with a cylindrical portion (12) brought into contact with the skin (Sk), a negative pressure generator (6) that generates a negative pressure inside the cylindrical portion (12) to cause the skin (Sk) to swell upward, and a detector (5) that detects that the skin (Sk) has been raised to a predetermined height inside the cylindrical portion (12).

25 Claims, 18 Drawing Sheets

FOREIGN PATENT DOCUMENTS

| | | |
|---|---|---|
| JP | 8-317918 | 12/1996 |
| JP | 2572823 | 3/1998 |
| JP | 2000-116629 | 5/2000 |
| JP | 2001-346781 | 12/2001 |
| WO | WO 01/64105 | 9/2001 |
| WO | WO 01/91634 | 12/2001 |
| WO | WO 0207599 A1 * | 1/2002 |

* cited by examiner

NEEDLE-INSERTION DEVICE

TECHNICAL FIELD

The present invention relates to a lancing apparatus for use in inserting a needle into the human skin for sampling a body fluid such as blood, or a tissue.

BACKGROUND ART

When treating diabetes patients, it is a common practice to measure the glucose concentration in blood sampled from the patient, for developing a treatment plan according to the measured value. Devices currently employed for such a purpose include a lancing apparatus according to JP-A 2001-346781, which is shown in FIG. 18A.

The lancing apparatus 9 shown therein includes a lancet 91 advanceably disposed in a cylindrical portion 90 of a housing with an opening at its outer end portion. The cylindrical portion 90 includes a flange portion 93 with a small hole 92 located at a central portion, and a glucose concentration meter 94 is disposed so as to project halfway into the hole 92. The lancing apparatus 9 also includes an electric pump (not shown) which, when activated, generates a negative pressure inside the cylindrical portion 90.

When using the lancing apparatus 9, upon activating the electric pump with the end portion of the cylindrical portion 90 brought into contact with a skin Sk, to thus generate a negative pressure inside the cylindrical portion 90, the skin Sk is caused to swell upward in the cylindrical portion 90. The swelling motion of the skin Sk is blocked by the flange portion 93. The lancet 91 automatically starts to move forward when a predetermined time has passed after the electric pump is activated, thus to stick into the skin Sk, thereby causing the skin Sk to bleed. The blood that has come out of the skin Sk is sampled by the glucose concentration meter 94, with an assistance of the negative pressure facilitating the skin to bleed. Accordingly, the lancing apparatus 9 is designed to sample a sufficient amount of blood for glucose concentration measurement, with a minimal insertion depth of the lancet 91.

However, the lancing apparatus 9 has the following drawbacks, originating from the setting that the lancet 91 automatically advances toward the skin Sk after driving the electric pump for a predetermined time.

In the lancing apparatus 9, the negative pressure may not be effectively acting on the skin Sk, after driving the electric pump for a predetermined time. For example, if the cylindrical portion 90 is improperly applied to the skin Sk so as to produce a gap between the cylindrical portion 90 and the skin Sk, air intrudes into the cylindrical portion 90 and interrupts the generation of the negative pressure. Also, even though the negative pressure is generated as expected, the swelling motion of the skin Sk largely depends on softness of the skin Sk.

For such reasons, the lancing apparatus 9 may fail to cause the skin Sk to sufficiently swell as shown in FIG. 18B, when there is a gap between the cylindrical portion 90 and the skin Sk, or when the skin Sk is not soft enough. If the lancet 91 is moved forward for insertion into the skin Sk under such a state, the lancet 91 may not reach the skin Sk, or may not be inserted deeply enough to provoke sufficient bleeding.

On the other hand, when the skin Sk is soft, although the skin Sk is sufficiently raised by the negative pressure, a portion Sk1 of the skin Sk may be tightly pressed against the flange portion 93 and depressed thereby, as shown in FIG. 18C. Such pressure against the skin Sk/Sk1 may lead to insufficient bleeding from the sticking point. In addition, another portion Sk2 indicated in FIG. 18C of the skin Sk may intrude into the small hole 92 because of the negative pressure, and may even protrude upward beyond the flange portion 93. In such a case the lancet 91 is inserted too deeply into the skin Sk, which not only causes a considerable damage on the skin Sk, but also makes the patient feel an intolerable pain.

DISCLOSURE OF THE INVENTION

It is an object of the present invention to enable proper insertion of an insertion element irrespective of softness of a skin, in a process wherein the skin is raised by a negative pressure for the insertion.

Accordingly, the present invention provides a lancing apparatus used for sampling a body fluid out of a skin by sticking an insertion element into the skin. The apparatus comprises a housing including a cylindrical portion brought into contact with the skin, and a negative pressure generator that generates a negative pressure inside the cylindrical portion to cause the skin to swell upward. The apparatus further comprises a detector that detects that the skin has been raised to a predetermined height inside the cylindrical portion.

For the negative pressure generator, an electric pump maybe employed. Obviously, a manual pump may also be employed.

Preferably, the lancing apparatus according to the present invention may further comprise a controller that performs a control so as to maintain a pressure inside the cylindrical portion within a specific range, after the detector has detected that the skin has been raised to the predetermined height. Such a lancing apparatus may further comprise a pressure detector that detects a pressure inside the cylindrical portion. In this case, the controller executes a control so as to maintain a pressure inside the cylindrical portion within a specific range, based on a pressure detected by the detector.

The specific range is defined by granting a specific tolerance to a reference pressure. It is preferable to determine the reference pressure at a lower value than the pressure inside the cylindrical portion at the time that the detector has detected that the skin has been raised to the predetermined height. Also, the upper limit and the lower limit of the specific range are preferably set at a lower value than the pressure inside the cylindrical portion at the time that the detector has detected that the skin has been raised to the predetermined height.

The detector may be capable of detecting a fluctuation of the swelling height of the skin. In this case, the controller controls the pressure inside the cylindrical portion so as to maintain the swelling height of the skin at a predetermined level. The detector may include a contacting member to which the skin contacts when the skin has been raised to the predetermined height. In this case, it is preferable that the detector can detect a contacting pressure of the skin applied to the contacting member, and that the controller controls the pressure inside the cylindrical portion so as to maintain the contacting pressure within a specific range.

The controller may control the operation of the negative pressure generator, so as to maintain a pressure inside the cylindrical portion within the specific range. The controller may also control an opening and closing action of a relief valve provided at a position communicating with the inside of the cylindrical portion, so as to maintain a pressure inside the cylindrical portion within the specific range. In this case, the controller may open the relief valve when the pressure inside the cylindrical portion becomes equivalent to or generally the same as the lower limit of the specific range. Various existing relief valves may be employed for use as the above relief valve.

Preferably, the lancing apparatus according to the present invention may further comprise a backup chamber into which a gas inside the cylindrical portion flows when the pressure inside the cylindrical portion becomes equivalent to or generally the same as the upper limit of the specific range, after generation of a negative pressure inside the cylindrical portion by the negative pressure generator. Such a backup chamber may be decompressed by the negative pressure generator.

The lancing apparatus according to the present invention may further comprise a gas supply selector controlled by the controller so as to select whether to supply a gas into the backup chamber. In this case, the lancing apparatus may further comprise a cylindrical portion pressure detector that detects a pressure inside the cylindrical portion, and the gas supply selector may be constituted of a relief valve opened or closed according to a detecting result given by the cylindrical portion pressure detector. In this case also, various existing relief valves may be employed.

The lancing apparatus according to the present invention may further comprise a backup chamber pressure detector that detects a pressure inside the backup chamber. In this case, it is preferable that the negative pressure generator decompresses the backup chamber, when the pressure detected by the backup chamber pressure detector exceeds a predetermined threshold value.

In the lancing apparatus according to the present invention, the cylindrical portion may include an attachment base to which a sampling element that samples a body fluid coming out of the skin by the insertion of the insertion element is removably attached. The sampling element may include an analyzing instrument.

It is preferable that the cylindrical portion of the housing is composed of a plurality of members, and one or more of the members are removable from another.

Preferably, the lancing apparatus according to the present invention may comprise a controller that controls a depth or speed of insertion of the inserting element into the skin, based on a pressure inside the cylindrical portion at the time that the detector has detected that the skin has been raised to the predetermined height.

BEST MODE FOR CARRYING OUT THE INVENTION

Figure 1:
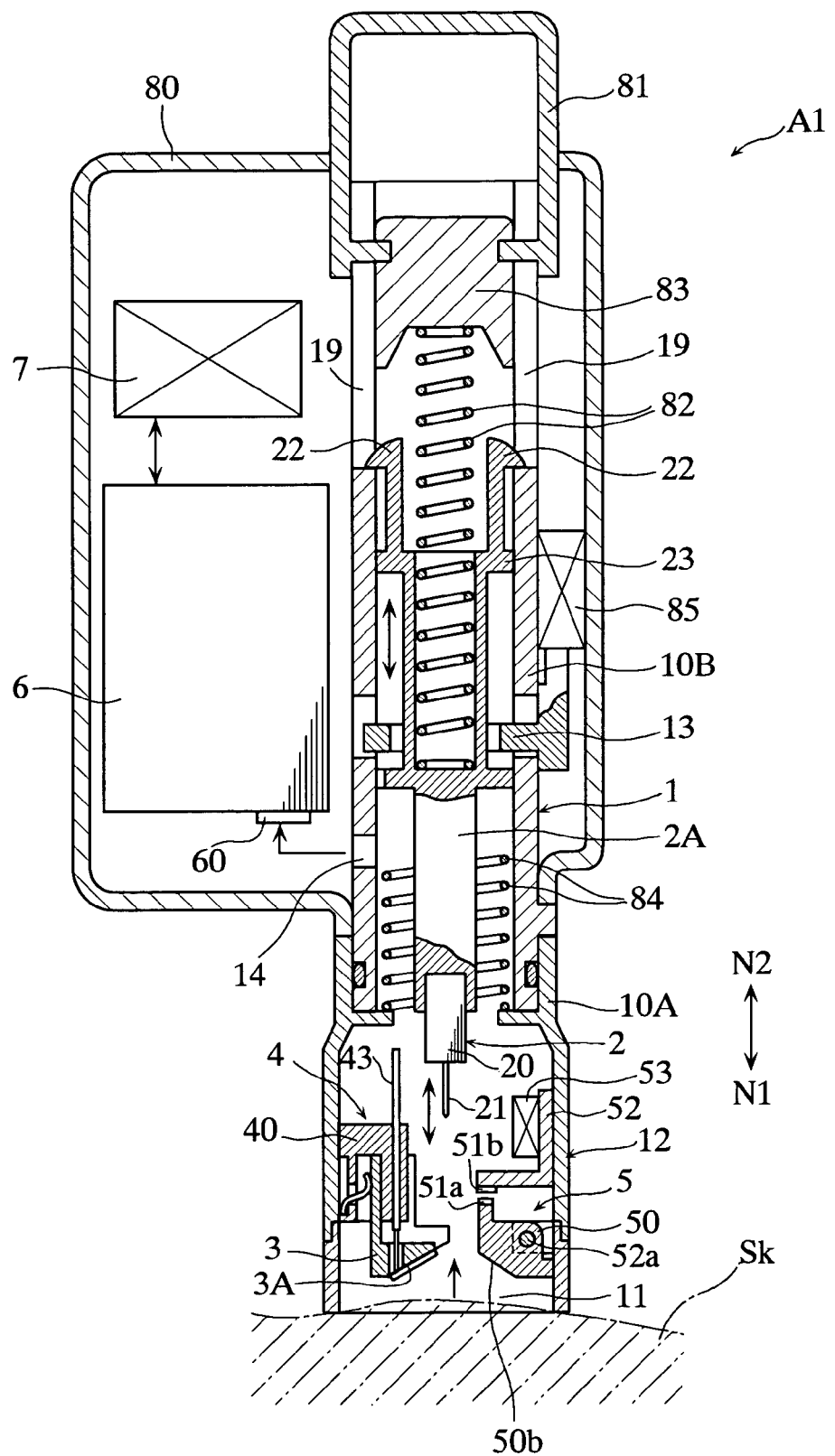
FIG. 1 is a cross-sectional view showing a lancing apparatus according to a first embodiment of the present invention.
Figure 2:
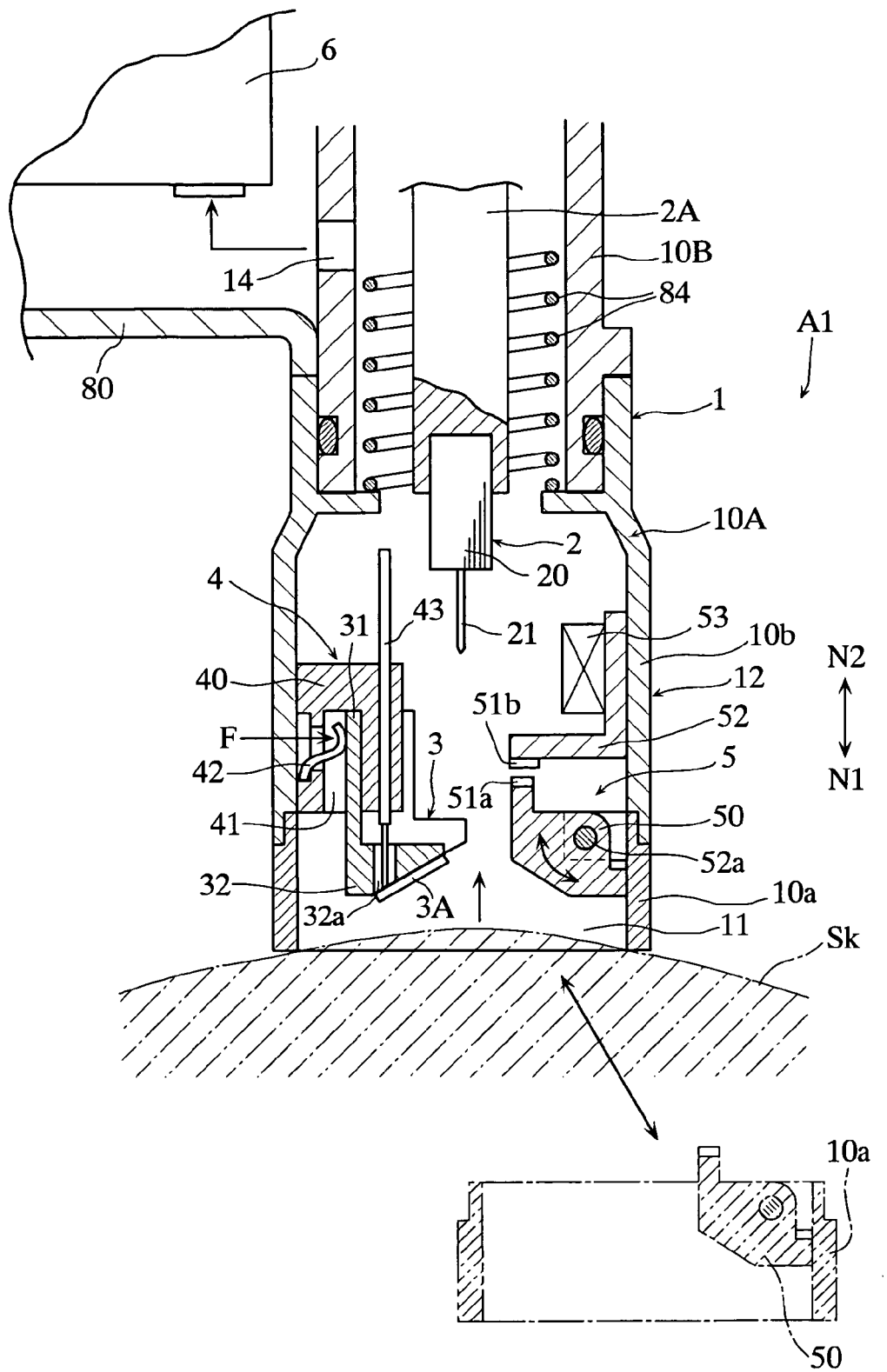
FIG. 2 is an enlarged fragmentary cross-sectional view taken from FIG. 1.

FIGS. 1 and 2 illustrate a lancing apparatus according to a first embodiment of the present invention. As explicitly shown in FIG. 1, the lancing apparatus A1 includes a housing 1, a lancet holder 2A that holds a lancet 2, an attachment base 4 to which a sensor holder 3 is attached, a detection switch 5, a pressure sensor 53, a pump 6, a control unit 7, and other components to be subsequently described.

The housing 1 is a combination of two sleeves 10A, 10B of a generally circular cylindrical shape, and a central portion and an upper portion in a direction of N1-N2 in FIG. 1 are enclosed in an outer case 80. In a portion close to the forward end of the housing 1 a cylindrical portion 12 with an opening 11 is provided, the forward end portion of which is brought into contact with a human skin Sk when using the lancing apparatus A1.

The sleeve 10A includes a first portion 10a and a second portion 10b. The first portion 10a supports a movable body 50 of the detection switch 5 to be described later, and is removable from the second portion 10b. Such a structure allows, for example when the movable body 50 is stained and needs cleaning, easily and properly cleaning the movable body 50 by simply removing the first portion 10a from the second portion 10b as indicated by an imaginary line in FIG. 1. When the first portion 10a is separated, the second portion 10b can also be easily cleaned.

The housing 1 includes a stopper 13 to be engaged with a flange portion 23 of the lancet holder 2A when the lancet holder 2A moves forward, so as to inhibit a farther travel of the lancet holder 2A. The stopper 13 is supported by an actuator 85, by which the position of the stopper 13 can be adjusted in a direction of N1-N2. Accordingly, moving the actuator 85 to select the position of the stopper 13 allows adjusting the advancing stroke of the lancet holder 2A, i.e. of the lancet 2, and thereby adjusting an insertion depth into the skin Sk.

The lancet 2 is constituted of a head portion 20 made of a synthetic resin, from which a metal needle 21 is projecting. The lancet holder 2A serves, when holding the lancet 2, to carry the lancet 2 in a direction of N1, i.e. toward the forward end of the housing 1. The lancet holder 2A is accommodated inside the housing 1 so as to reciprocatively move in a direction of N1-N2, and latched with the housing 1, to be released to move forward once the latch is disengaged.

More specifically, when the lancet holder 2A is moved in a direction of N2, a latch hook 22 gets engaged with a cutaway portion 19 of the housing 1, so that the lancet holder 2A gets latched with the housing 1. The lancet holder 2A can be caused to move in a direction of N2 at the same time when pressing the lancet 2 into the lancet holder 2A. As a matter of course, the lancet holder 2A may be latched with the housing 1 independently from the step of pressing the lancet 2 into the lancet holder 2A.

Figure 5:
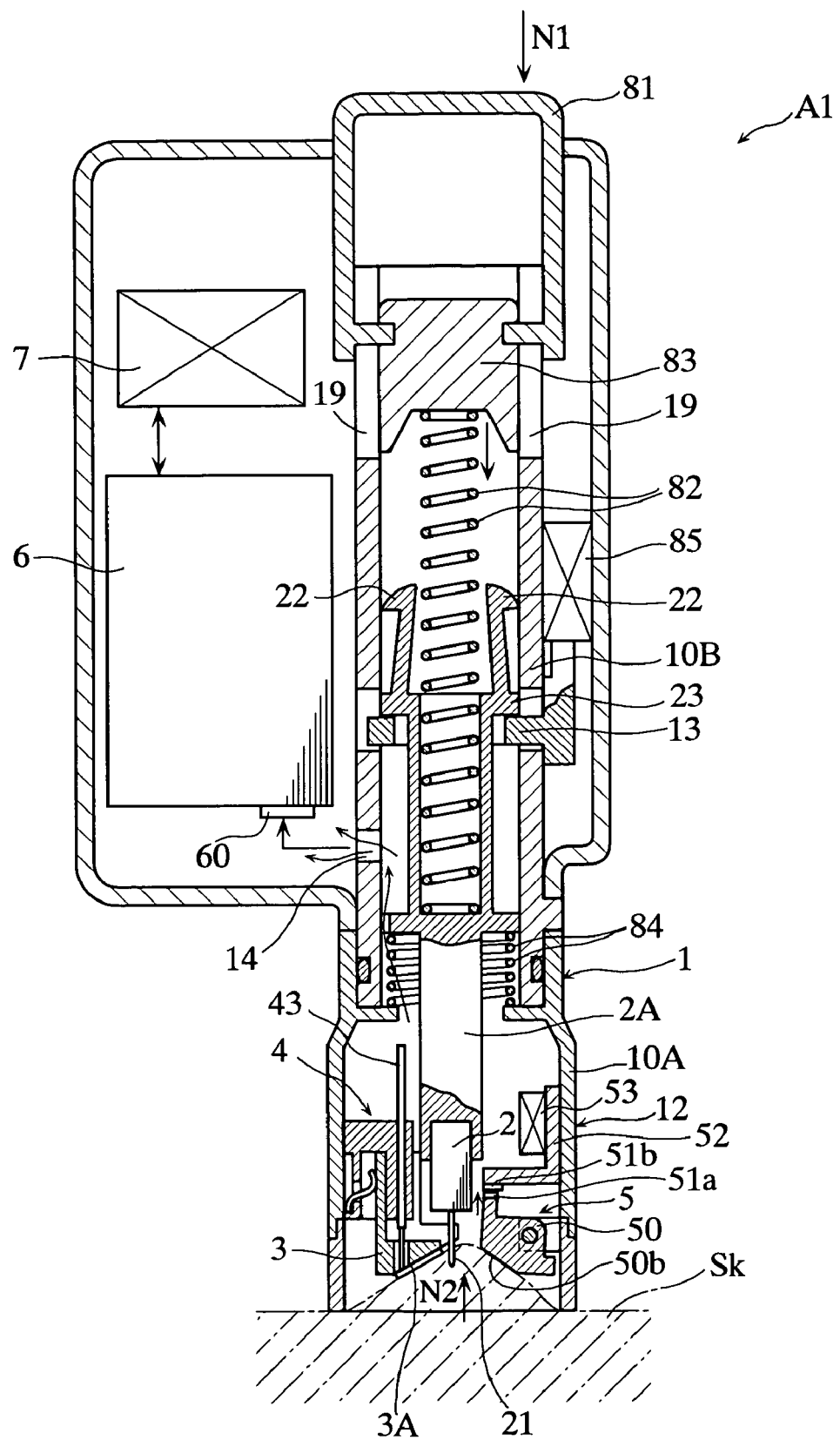
FIG. 5 is a cross-sectional view showing the lancing apparatus of FIG. 1 in operation.

Referring now to FIG. 5, when an operating cap 81 is moved in a direction of N1 with the lancet holder 2A latched with the housing 1, a latch releasing pusher 83 moves forward compressing a spring 82, thus to disengage the latch hook 22 from the cutaway portion 19. This causes the lancet holder 2A to be pressed forward by the spring force of the spring 82 together with the lancet 2, so that a needle 21 of the lancet 2 sticks into the skin Sk. The lancet holder 2A can move forward until the flange portion 23 of the lancet holder 2A contacts the stopper 13 of the housing 1, which inhibits the lancet holder 2A from advancing farther. When the lancet holder moves forward a return spring 84 is compressed, so that the spring force of the return spring 84 presses backward the lancet holder 2A by an appropriate distance, once the lancet holder 2A has finished moving forward. This action causes the needle 21 of the lancet 2 to be pulled out of the skin Sk.

The pump 6 is an electric pump capable of aspiring and discharging air, located inside the outer case 80 at a position adjacent to the housing 1. An intake port 60 of the pump 6 is connected to a communication port 14 provided on a sidewall of the housing 1, so that when the pump 6 is activated a negative pressure is generated inside the cylindrical portion 12. When a negative pressure is generated with the cylindrical portion disposed in contact with the skin, the negative pressure acts on the skin Sk, so as to cause the skin to swell upward inside the cylindrical portion 12. The pump is driven for example by a battery not included in the drawing.

The attachment base 4, which serves as a base for removably attaching the sensor holder 3, includes an attachment 40 made of a synthetic resin, fixed to an inner wall of the cylindrical portion 12. The sensor holder 3 is a disposable component that serves to retain a biosensor 3A. The lancet 2 and the biosensor 3A are disposable as well.

Figure 4A:
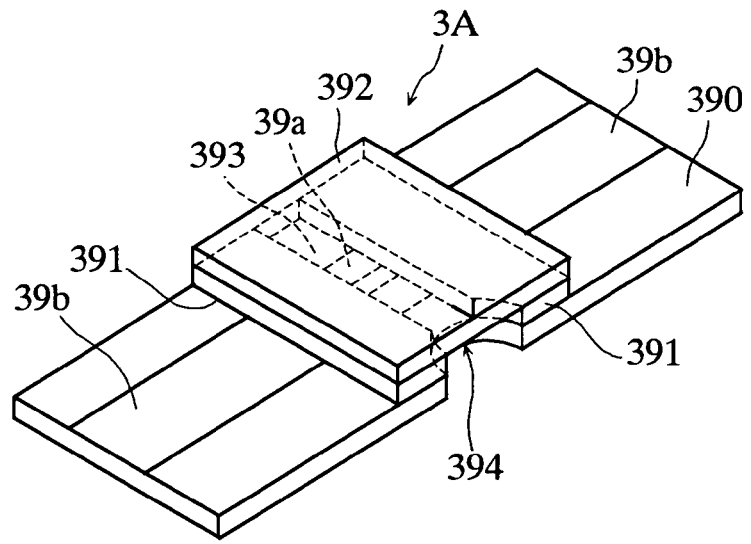
FIG. 4A is a perspective view showing an assembled biosensor attached to the sensor holder.
Figure 4B:
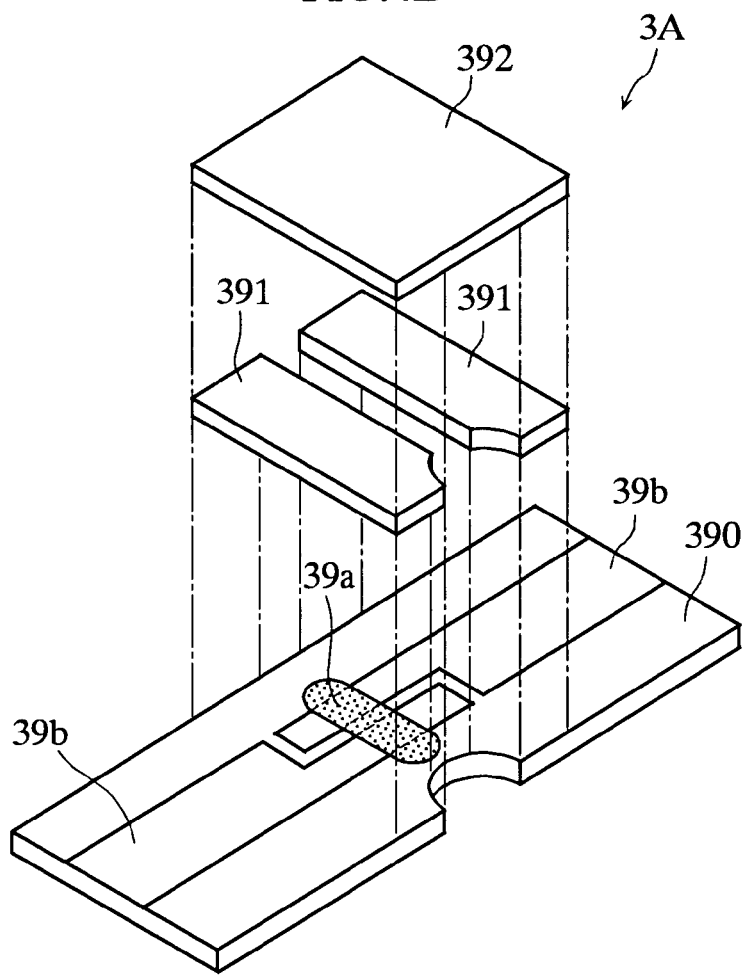
FIG. 4B is an exploded perspective view of the biosensor of FIG. 4A.

The biosensor 3A includes, as shown in FIGS. 4A and 4B, a reagent portion 39a containing an enzyme that performs a certain reaction (for example oxidation) with glucose in blood and a pair of electrodes 39b, on a surface of a substrate 390. On the substrate 390, a pair of spacers 391 is disposed with a gap therebetween, and a cover plate 392 that covers the spacers is stacked thereon, which constitute a capillary 393 as a whole. The substrate 390 and the spacers 391 are provided with a recess 394 of a matching shape that serves as a blood inlet. Thus the biosensor 3A is designed such that when blood is introduced into the recess 394 the blood is led through the capillary 393 by a capillary effect, to thereby reach the reagent portion 39a.

Figure 3:
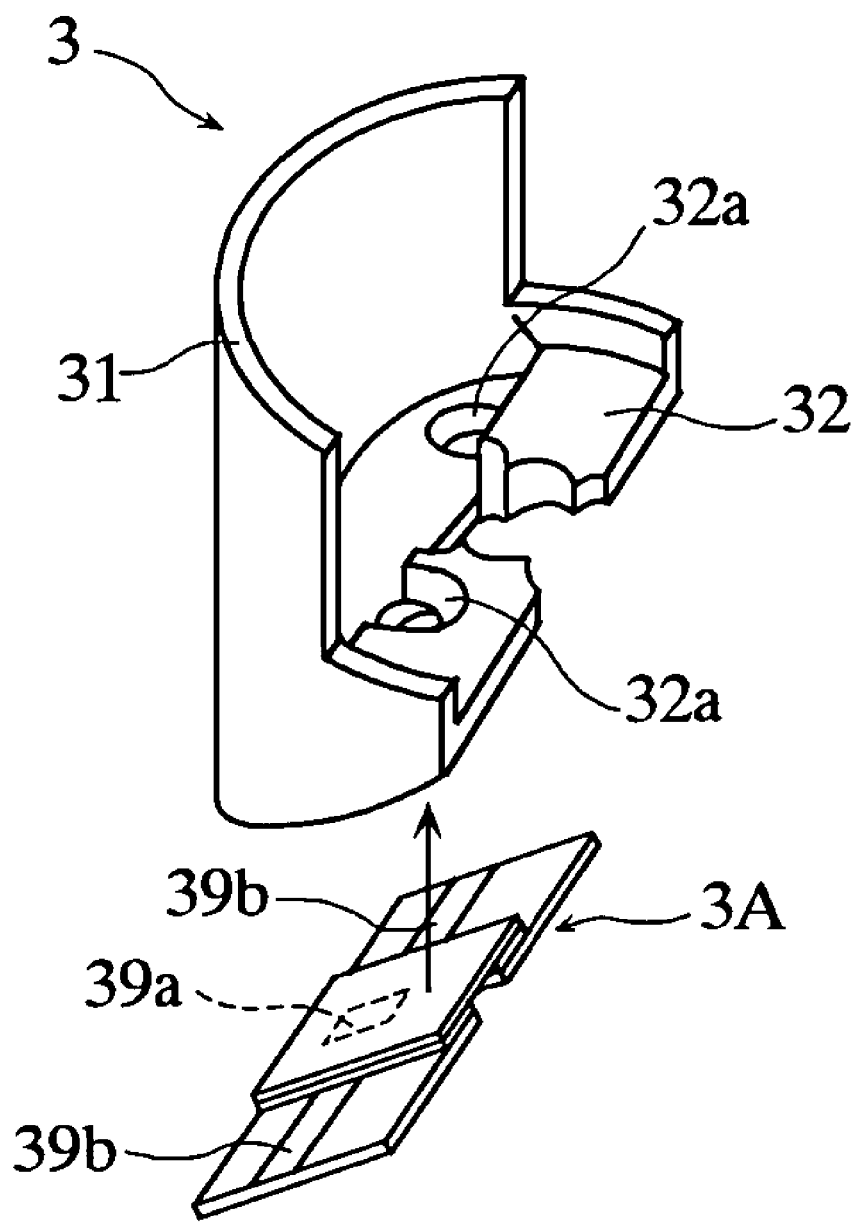
FIG. 3 is a perspective view showing a sensor holder.

Referring to FIGS. 2 and 3, the sensor holder 3 is made of a synthetic resin, and includes a main body 32 and a sidewall portion 31, having an arc-shaped cross section and erecting upward from the main body 32. The bottom face of the main body 32 is inclined, and this is where the biosensor 3A is attached. The sensor holder 3 can be attached to and removed from the attachment base 4 through the opening 11 of the cylindrical portion 12. More specifically, as explicitly shown in FIG. 2, the attachment base 4 has a hollow portion 41 with an opening facing downward, so that when the sidewall portion 31 of the sensor holder 3 is inserted from below into the hollow portion 41 the sensor holder 3 is retained by a pressing force F of a spring 42. The sensor holder 3 may be attached to the attachment base 4 by providing an engaging mechanism that allows attaching and removing, between the sensor holder 3 and the attachment base 4.

The attachment base 4 also holds a pair of measuring probes 43 extending along a direction of N1-N2 of the housing 1. The drawings only show one of the measuring probes 43. The measuring probes 43 are inserted through a pair of holes 32a provided on the sensor holder 3, so as to contact the pair of electrodes 39b on the biosensor 3A. In other words, the pair of measuring probes 43 can apply a voltage to the biosensor 3A, and measure a current running therein. The current value measured by the pair of probes 43 serves as a base for calculation of a glucose concentration in the blood introduced to the capillary 393 (Ref. FIG. 4A) of the biosensor 3A, by the control unit 7 as will be subsequently described.

The detection switch 5 is located inside the cylindrical portion 12, and includes a movable body 50 and a bracket 52, respectively provided with a switch terminal 51a, 51b. The movable body 50 is pivotally supported by a shaft 52a of the bracket 52, so as to shift the position of the switch terminal 51a. The movable body 50 has a downwardly tapered face 50b.

Figure 6:
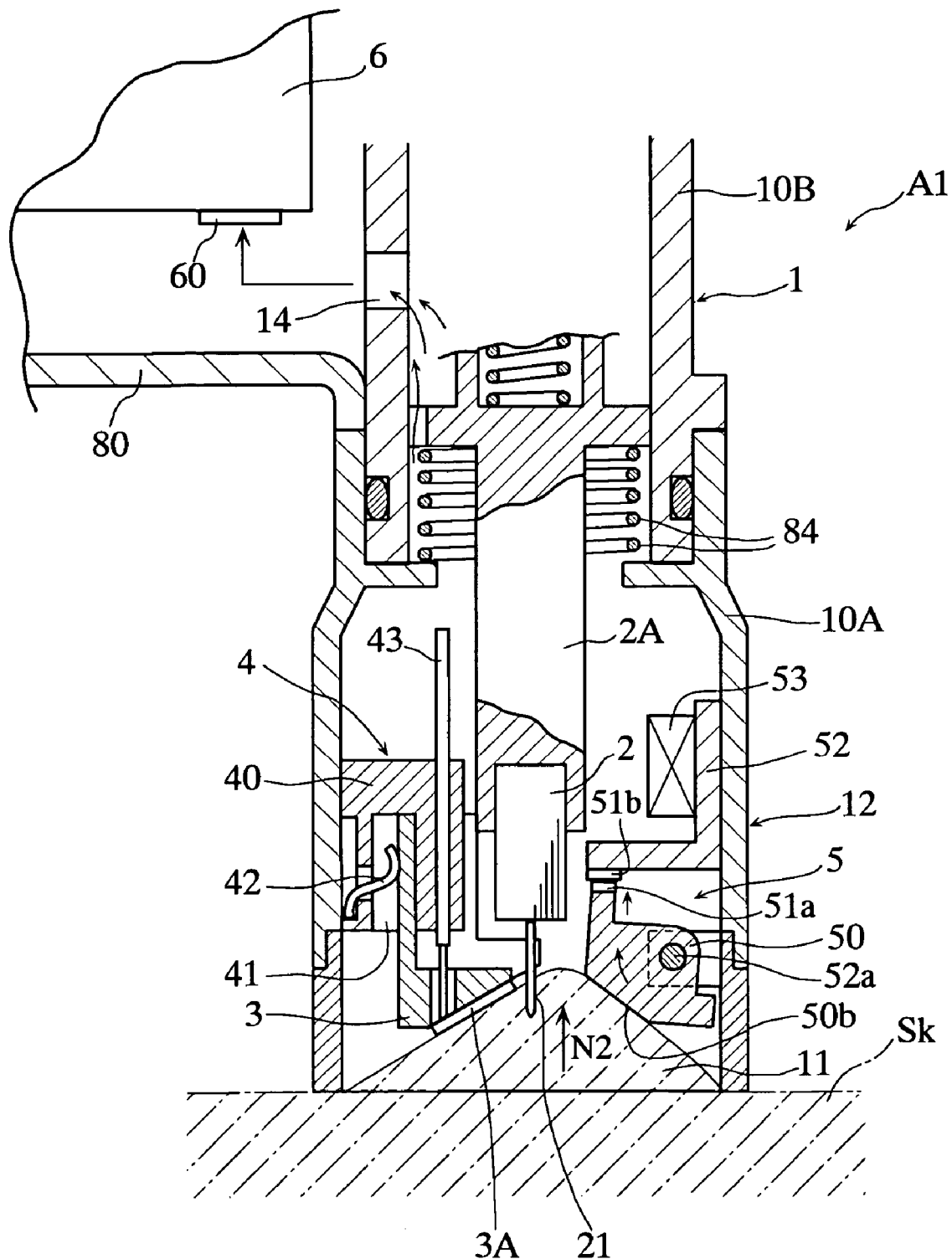
FIG. 6 is an enlarged fragmentary cross-sectional view taken from FIG. 5.

In the detection switch 5, as shown in FIGS. 5 and 6, when the skin Sk swells upward inside the cylindrical portion 12 in a direction of N2, the movable body 50 is lifted by the skin Sk, thus to rotate upward. By this action the switch terminal 51a of the movable body 50 is shifted upward, and contacts the switch terminal 51b of the bracket 52. This turns the detection switch on, and a signal to this effect is input to the control unit 7. Also, since the movable body 50 has a tapered face 50b, the skin Sk generally evenly contacts the tapered face 50b and the bottom face of the sensor holder 3, when the skin Sk swells upward.

The pressure sensor 53, which serves to detect a pressure inside the cylindrical portion 12, is located inside the cylindrical portion 12. The pressure sensor 53 transmits data of the detected pressure to the control unit 7.

The control unit 7 includes, for example a CPU and an associated memory, and is located at an appropriate position inside the outer case 80. The control unit 7 controls the activation of the pump 6, the positioning of the stopper 13 and so on to be described later, based on the on signal from the detection switch 5, the pressure data detected by the pressure sensor 53 and so forth. The control unit 7 can also calculate the glucose concentration in the blood introduced to the capillary 393 (Ref. FIG. 4A) of the biosensor 3A.

Although not shown in the drawings, the lancing apparatus A1 is also provided with a display device such as an LCD panel, for example on a surface of the outer case 80, which displays the glucose concentration value calculated by the control unit 7, and other data. The lancing apparatus A1 further includes operating switches (not shown) for turning on and off the power source of the control unit 7, the pump 6 and so on.

Figure 7:
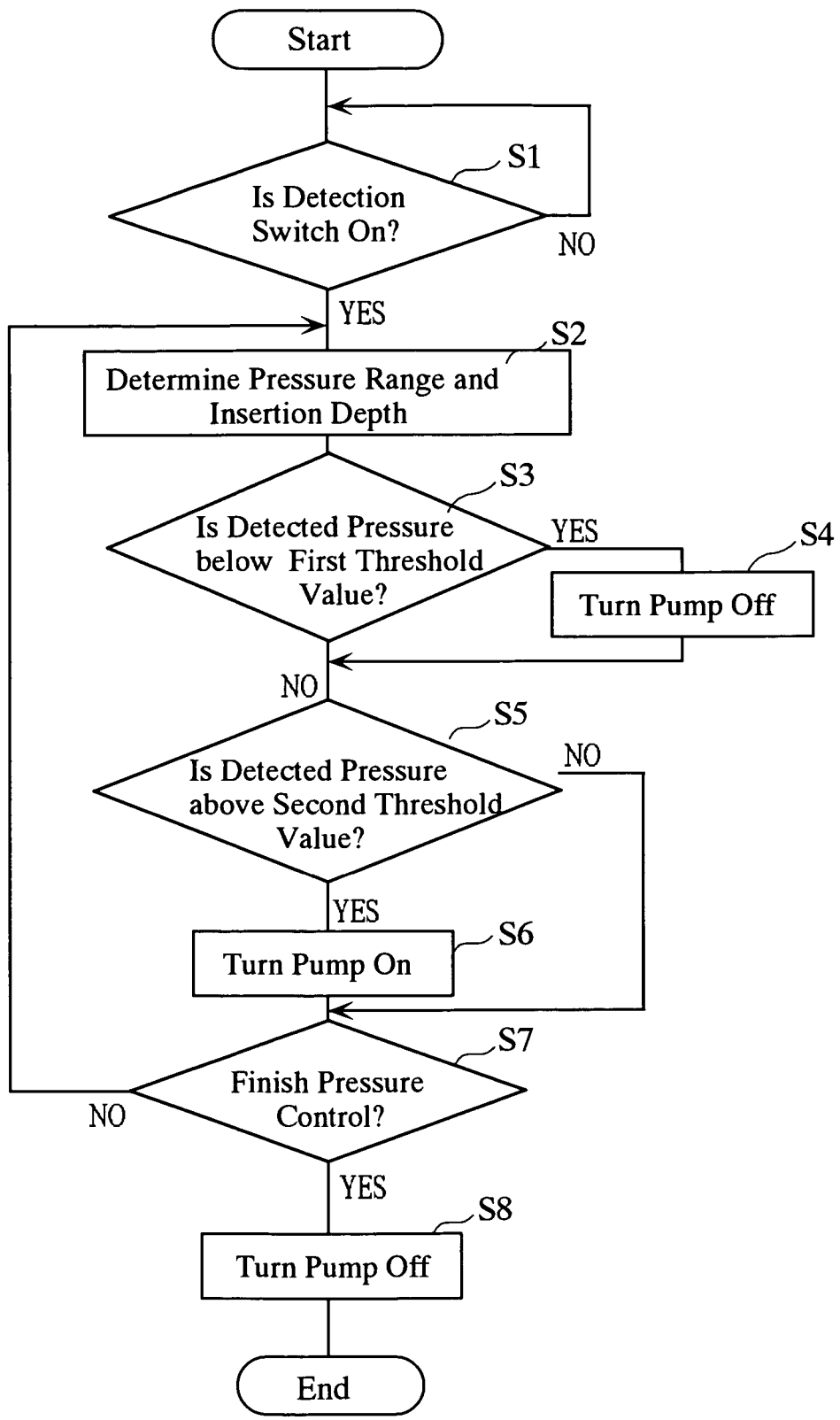
FIG. 7 is a flowchart for explaining a controlling process for a pressure inside a cylindrical portion, performed by a control unit of the lancing apparatus of FIG. 1.

Now referring to FIG. 7 showing an example of the controlling process of the control unit 7, an operation of the lancing apparatus A1 will be described.

When using the lancing apparatus A1 to stick the needle into the human skin Sk, the cylindrical portion 12 is first applied to the skin Sk which is the object of the insertion as shown in FIGS. 1 and 2, and then the operating switch is manipulated so as to activate the pump 6. This generates a negative pressure inside the cylindrical portion, by which the skin Sk swells upward.

Then the control unit 7 decides whether the detection switch is on (S1). As already stated, the detection switch is turned on when the skin Sk is raised to a predetermined height. Accordingly, checking whether the detection switch 5 is turned on leads to judging whether the skin Sk has been raised to a predetermined height.

When the control unit 7 decides that the detection switch 5 is not on (i.e. is off) (NO at S1), the control unit 7 repeats the step of S1 until the detection switch 5 is decided to be on (YES at S1).

In the case where the detection switch 5 is not decided to be on (NO at S1) despite repeating the step of S1 over a predetermined times, or despite that a predetermined time has elapsed after starting the judgment of S1, the control unit 7 may suspend the step of S1 and perform an error process. In such a case it is preferable that the control unit 7 displays to this effect on the display device, or activates an alarm sound. This facilitates the user to notice that he/she has not properly placed the cylindrical portion 12 on the skin Sk and thus failed to apply sufficient negative pressure to the skin Sk, thereby exempting the user from sticking the needle to the skin Sk despite that the skin Sk has not been sufficiently raised.

Upon deciding that the detection switch 5 is on (YES at S1), the control unit 7 decides a pressure range inside the cylindrical portion 12 that serves as the controlling target (S2), so as to maintain the pressure inside the cylindrical portion 12 within a certain range. At S2, the needle insertion depth is also determined along with the decision of the target pressure range.

Figure 8:
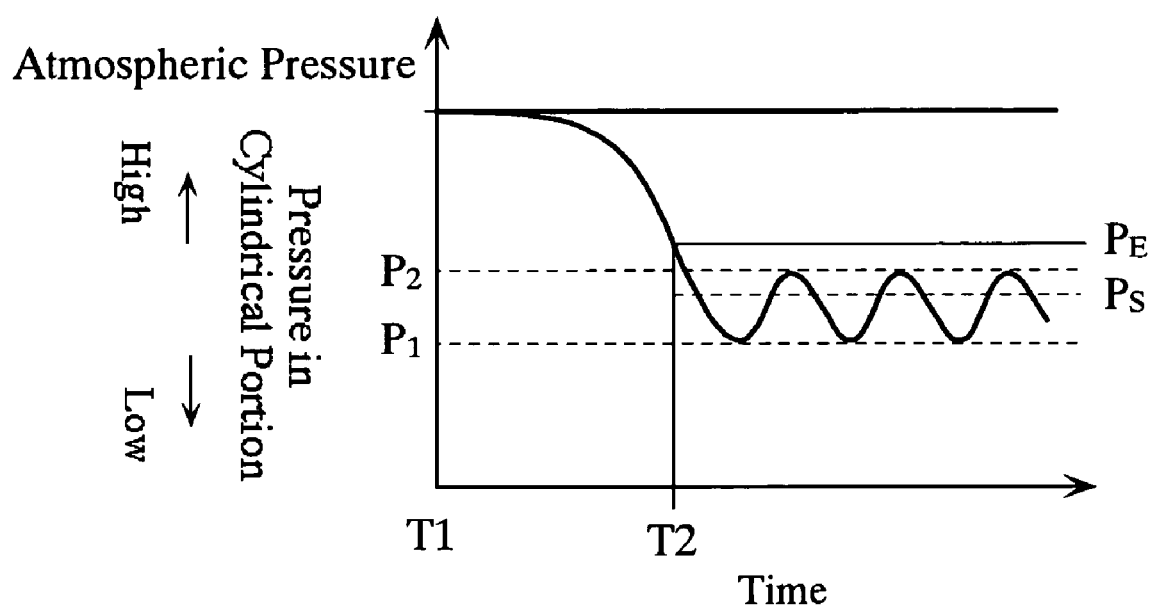
FIG. 8 is a line graph showing a pressure fluctuation inside the cylindrical portion.

The target pressure range may be defined, as shown in FIG. 8, by first establishing a reference pressure $P_S$ at a level slightly lower (for example 20 to 30 gf/cm$^2$) than the actual pressure $P_E$ inside the cylindrical portion 12 at the time that the detection switch 5 has been turned on, and determining a first threshold value $P_1$ and a second threshold value $P_2$ which are lower and higher than the reference pressure $P_S$ by an appropriate value respectively, as the lower limit and the upper limit of the target pressure range. It is preferable to set the first threshold value $P_1$ and the second threshold value $P_2$ at a lower value than the actual pressure $P_E$ inside the cylindrical portion 12 at the time that the detection switch 5 has been turned on.

The needle insertion depth may be determined through the positioning of the stopper 13, based on the pressure inside the cylindrical portion 12 detected by the pressure sensor 53. In other words, the control unit 7 drives the actuator 85 to move the stopper 13 such that the lower the detected pressure is, the farther forward the lancet 2 moves so as to insert the needle deeper.

Adopting the system of adjusting the needle insertion depth according to the detected pressure provides the following advantage. As a general tendency, while a stiffer skin gives less amount of blood from the insertion point, while a stiffer skin can less readily be raised. Whereas, in the lancing apparatus A1, the pressure inside the cylindrical portion 12 at the moment that the detection switch 5 is turned on becomes lower when the skin Sk is stiffer. Accordingly, increasing the needle insertion depth into the skin Sk for a lower detected pressure (i.e. for a stiffer skin) results in obtaining a generally constant amount of blood by the needle insertion, irrespective of the stiffness of the skin Sk.

Such advantage can also be attained when adopting a system of adjusting a needle insertion speed according to the stiffness of the skin, i.e. the detected pressure $P_E$ (Ref. FIG. 8). More specifically, when the detection switch 5 is turned on upon detecting that the skin Sk has been raised to a predetermined height by the negative pressure, the control unit 7 may look up the pressure $P_E$ (Ref. FIG. 8) detected at that moment by the pressure sensor 53, to thereby control the advancing speed of the lancet 2 for the insertion to be slower, when the pressure $P_E$ is lower (i.e. when the skin Sk is stiffer). In general, the slower the lancet 2 moves, the larger wound is made at the insertion point on the skin Sk and hence the more amount of blood is obtained, provided that the needle insertion depth is the same. Therefore, the system of adjusting a needle insertion speed according to the detected pressure $P_E$ (Ref. FIG. 8) also allows obtaining a generally constant amount of blood irrespective of the stiffness of the skin Sk.

For adjusting the advancing speed of the lancet 2, for example a member that makes a sliding contact with the lancet 2 or the lancet holder 2A when the lancet 2 moves forward may be provided, with a mechanism that adjusts the frictional force generated by the sliding motion of those components.

Upon deciding the target pressure range and the needle insertion depth (S2), the control unit 7 decides whether the pressure inside the cylindrical portion 12 detected by the pressure sensor 53 is lower than the first threshold value $P_1$ (S3). Upon deciding that the detected pressure is lower than the first threshold value $P_1$ (YES at S3), the control unit 7 stops driving the pump 6 (S4). This prevents the pressure inside the cylindrical portion 12 from becoming unduly lower than the first threshold value $P_1$ so that the skin Sk would be excessively depressed. If the control unit 7 decides that the detected pressure is not lower (i.e. is higher) than the first threshold value $P_1$ (NO at S3), the control unit 7 keeps driving the pump 6.

The control unit 7 then decides whether the detected pressure is higher than the second threshold value $P_2$ (S5). The step S5 serves to detect a phenomenon that after stopping the pump 6 a fine gap is produced between the cylindrical portion 12 and the skin Sk, and hence air intrudes into inside of the cylindrical portion 12 through such a gap, which results in an increase in pressure inside the cylindrical portion 12 and insufficient swelling of the skin Sk.

Upon deciding that the detected pressure is higher than the second threshold value $P_2$ (YES at S5), the control unit 7 activates the pump 6 (S6). This makes up the lack of negative pressure inside the cylindrical portion 12, thereby causing the skin Sk to sufficiently swell upward. If the control unit 7 decides that the detected pressure is not higher (i.e. is lower) than the second threshold value $P_2$ (NO at S5), the control unit 7 leaves the pump 6 stopped.

Further the control unit 7 decides whether to finish the pressure control inside the cylindrical portion 12 (S7). In other words, the control unit 7 decides whether the pressure inside the cylindrical portion 12 still needs to be controlled, i.e. for example whether the needle insertion has been completed. If the control unit 7 decides not to finish controlling the pressure inside the cylindrical portion 12 (i.e. the pressure inside the cylindrical portion 12 needs control) (NO at S7), the control unit 7 repeats the steps of S2 to S7 until the control unit 7 decides that the pressure control inside the cylindrical portion 12 no longer has to be controlled (YES at S7).

It is preferable that the control unit 7 announces the results of the steps S1 to S7 during the performance of these steps. Such announcement may be visually made on the display device or audibly made by a sound. This facilitates the user to assume that the skin Sk is being properly raised, by confirming the announcement to that effect. Accordingly, the user can press the operating cap 81 thus to insert the needle into the skin Sk, finding the appropriate timing that the skin Sk has been correctly raised.

When the skin Sk bleeds by the insertion of the needle, the blood is taken up as a sample by the biosensor 3A. On the biosensor 3A, glucose in the blood reacts with the reagent portion 39a in the capillary 393 (Ref. FIG. 4A). At this moment, applying a voltage across the pair of electrodes 39b on the biosensor 3A from the pair of measuring probes 43 of the lancing apparatus A1 allows measuring a response current value reflecting the glucose concentration, with the pair of measuring probes 43. The control unit 7 calculates the glucose concentration based on the response current value, and the result is for example shown on the display device. Therefore, since the lancing apparatus A1 can also calculate and display the glucose concentration in addition to the needle insertion function, the user can enjoy a greater benefit.

Now, upon deciding that it is no longer necessary to control the pressure inside the cylindrical portion 12 (YES at S7), the control unit 7 turns off the pump 6 (S8) and finishes the controlling operation of the pressure inside the cylindrical portion 12.

During the foregoing control process, when the pump is activated at the time T1, the pressure inside the cylindrical portion 12 gradually drops, as the example shown in FIG. 8. After the skin Sk has been sufficiently raised thus to turn the detection switch 5 on at the time T2, the pressure inside the cylindrical portion 12 is maintained between the first threshold value $P_1$ and the second threshold value $P_2$ below and above the reference pressure $P_S$, until the needle insertion has been completed. Accordingly, since the pressure inside the cylindrical portion 12 can be maintained within a predetermined range (between the first threshold value $P_1$ and the second threshold value $P_2$) until the needle insertion has been completed, the swelling height of the skin Sk can also be maintained within a certain range.

Also, the first threshold value $P_1$ and the second threshold value $P_2$ are determined based on the actual pressure $P_E$ inside the cylindrical portion 12 at the time that the detection switch 5 has been turned on, which is exactly the pressure at the time that the skin Sk has been raised to a predetermined level. Accordingly, the pressure $P_E$ substantially reflects the softness of the skin Sk. Therefore, in the lancing apparatus A1, since the target pressure range (between the first threshold value $P_1$ and the second threshold value $P_2$) controlled by the control unit 7 is defined for each needle insertion performance according to the softness of the skin Sk, the swelling height of the skin Sk can be maintained within a certain range, irrespective of the softness of the skin Sk. This enables the lancing apparatus A1 to insert the needle 21 constantly to an appropriate depth. Consequently, the needle 21 can be kept from being inserted too deeply because of excessive swelling of the skin Sk when the skin Sk is soft. Likewise, the needle 21 can be prevented from being insufficiently inserted into the skin Sk, because of insufficient swelling of the skin Sk when the skin Sk is stiff. Obviously, since a negative pressure is acting inside the cylindrical portion 12, the bleeding from the skin Sk can be thereby facilitated. Based on all such aspects, the lancing apparatus A1 can obtain a necessary and sufficient amount of blood for the measurement of glucose concentration by the biosensor 3A, without giving an undue damage to the skin Sk.

In addition, since the target pressure range inside the cylindrical portion 12 is set to be lower than the pressure $P_E$ inside the cylindrical portion 12 at the time that the detection switch 5 has been turned on, the skin Sk does not drop from the level at the time that the detection switch 5 has been turned on, and hence the detection switch 5 is maintained on. Accordingly, the user is not bothered by unpleasant repetition of the switching noise of the detection switch 5. Further, the target pressure range includes a reference pressure $P_S$ which is slightly lower (for example 20 to 30 gf/cm$^2$) than the actual pressure $P_E$ inside the cylindrical portion 12 at the time that the detection switch 5 has been turned on, and the first threshold value $P_1$ and the second threshold value $P_2$ which are lower and higher than the reference pressure $P_S$ by an appropriate value respectively, as the lower limit and the upper limit of the target pressure range. Accordingly, since a relatively weak force is applied to the skin Sk when the skin Sk is contacting the movable body 50 or the biosensor 3A, the blood flow at the contacting portion is barely disturbed, and consequently the bleeding from the skin Sk is not disturbed.

FIGS. 9 through 17 illustrate different embodiments of the present invention. In these drawings, constituents that are the same as or similar to those of the first embodiment are given an identical numeral, and duplicating description will be omitted.

Figure 9:
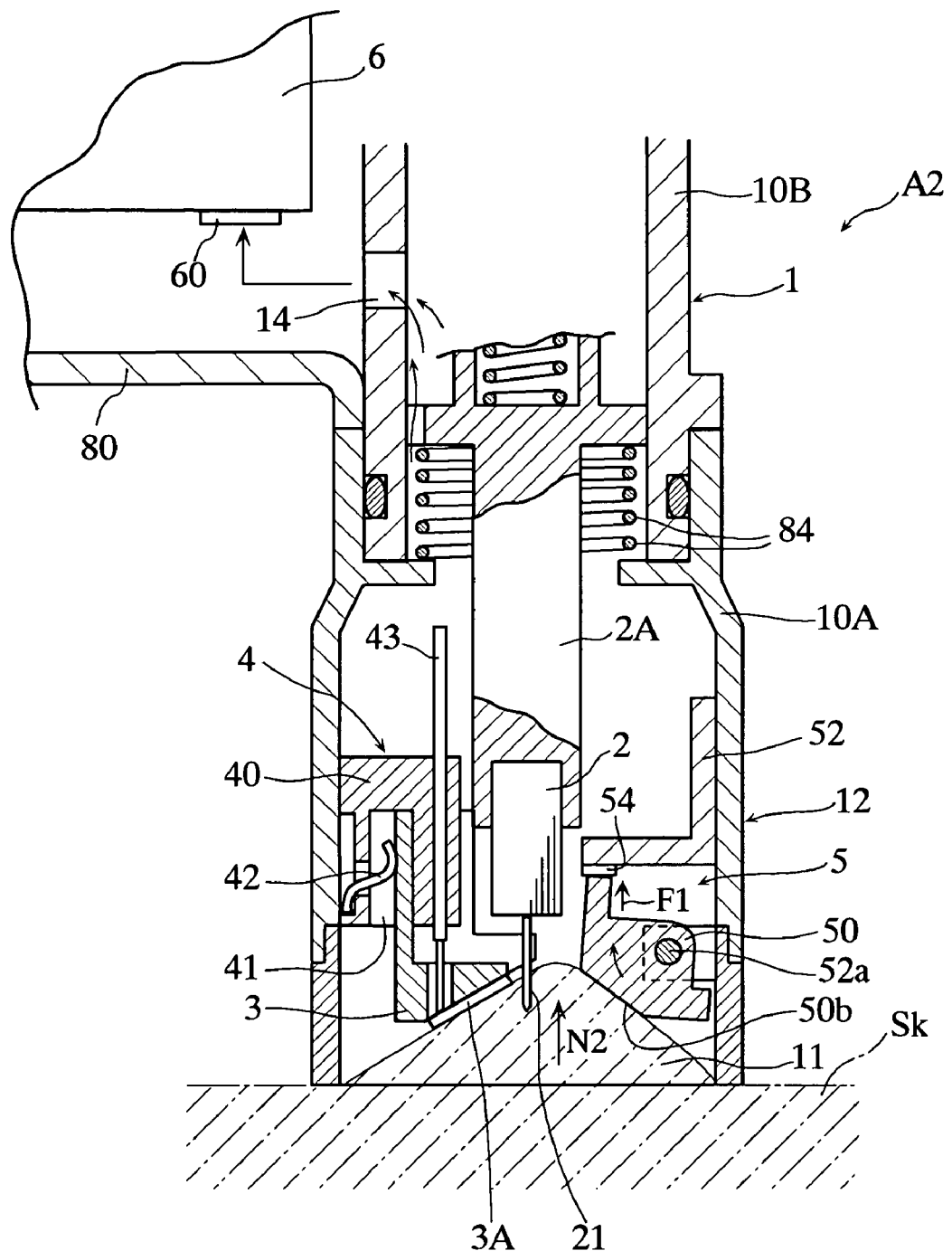
FIG. 9 is an enlarged fragmentary cross-sectional view showing a lancing apparatus according to a second embodiment of the present invention.

FIG. 9 depicts a lancing apparatus according to a second embodiment. In the lancing apparatus A2 shown therein, the detection switch 5 is provided with a load sensor 54. The load sensor 54 is attached to the bracket 52, and detects a load F1 applied thereto when pressed by the movable body 50 because of the swelling motion of the skin Sk. The load sensor 54 may be attached to the movable body 50 instead.

Load data detected by the load senor 54 is input to the control unit 7 (not shown in FIG. 9, but in FIG. 1). The control unit 7 in the lancing apparatus A2 performs the following control to maintain the swelling height of the skin Sk at a generally constant level.

Figure 10:
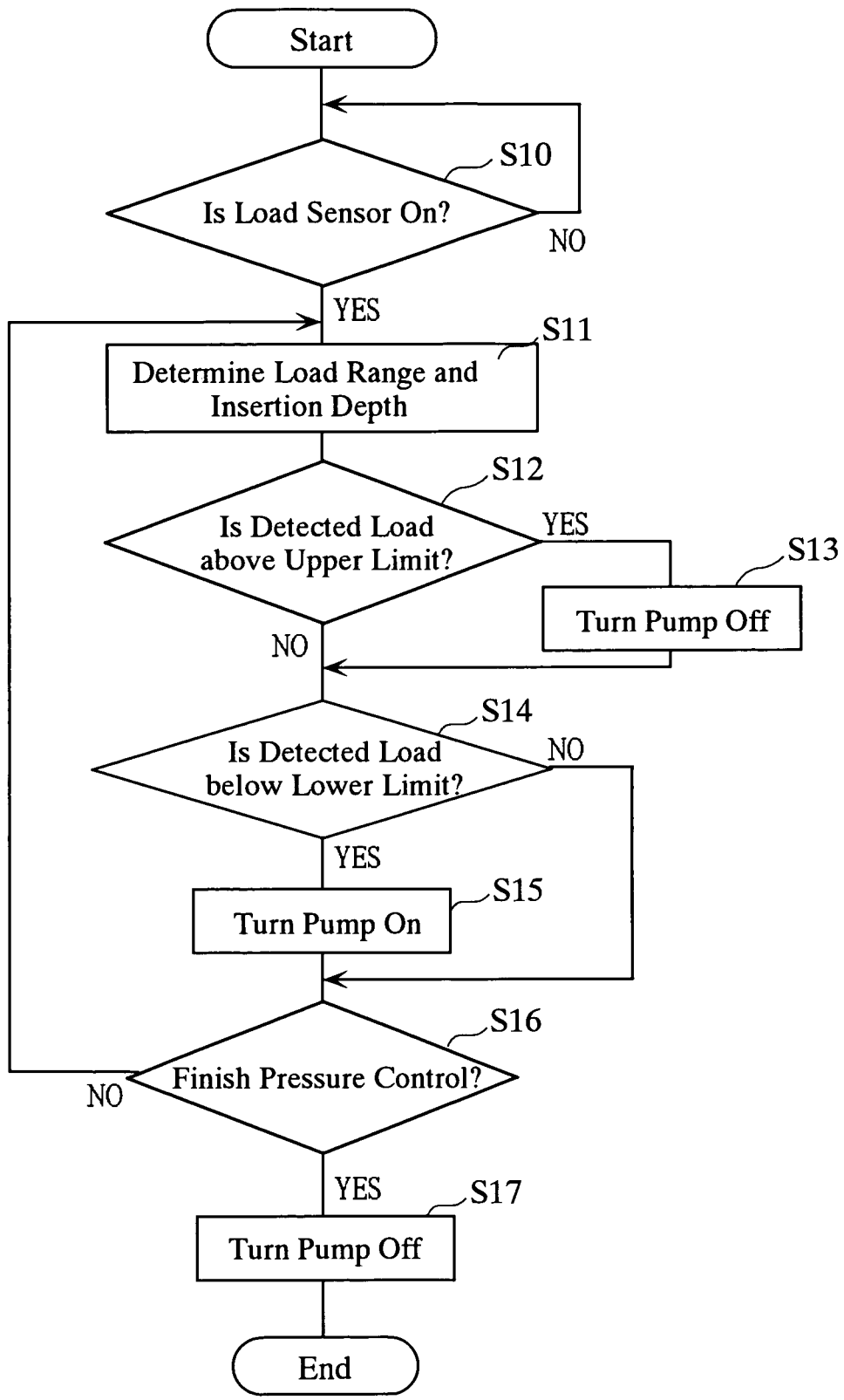
FIG. 10 is a flowchart for explaining a controlling process for a pressure inside a cylindrical portion, performed by a control unit of the lancing apparatus of FIG. 9.
Figure 11:
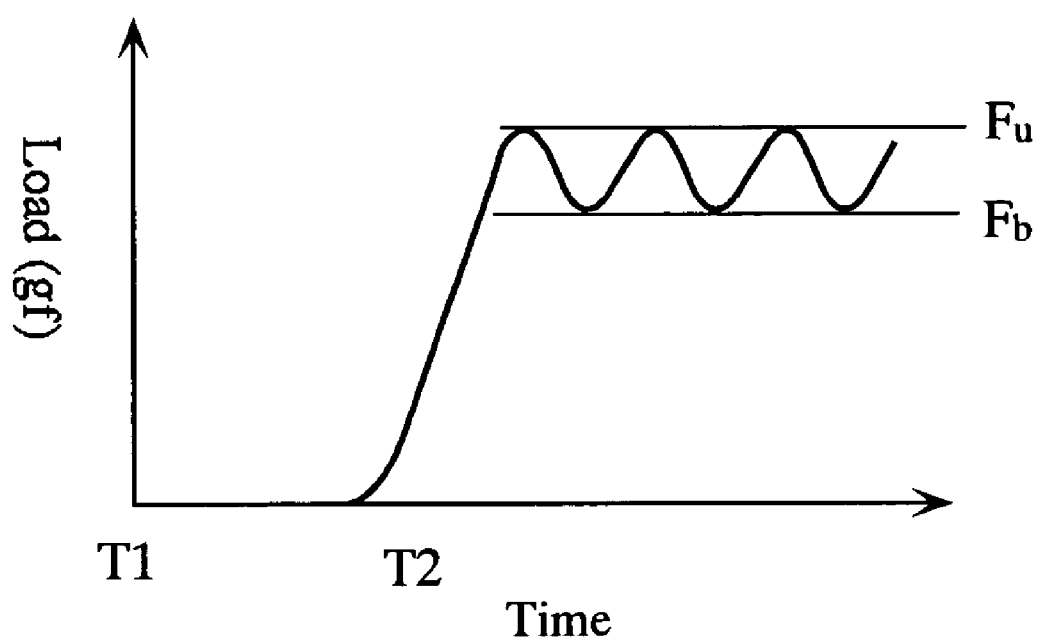
FIG. 11 is a line graph showing a pressing load fluctuation detected by a load sensor of the lancing apparatus of FIG. 9.

Referring to the flowchart according to FIG. 10, when the control unit 7 decides that the load sensor 54 has been turned on pressed by the movable body 50 (YES at S10), the control unit 7 defines a load range (between an upper limit $F_u$ and a lower limit $F_b$ shown in FIG. 11) that serves as a target of the control (S11). At S11, the needle insertion depth is also determined along with the decision of the target load range, according to an output of the load sensor 54.

If the control unit 7 decides that the load sensor 54 has not yet been sufficiently pressed by the movable body 50 to be turned on (NO at S10), the control unit 7 repeats the step of S10 until the load sensor 54 is decided to have been turned on pressed by the movable body 50 (YES at S10).

Upon establishing the target load range (S11), the control unit 7 monitors the load being detected by the load sensor 54, and decides whether the load is above the upper limit $F_u$ (Ref. FIG. 11) (S12). When the control unit 7 decides that the load is above the upper limit $F_u$ (Ref. FIG. 11) (YES at S12), the control unit 7 stops driving the pump 6 (S13).

Upon stopping driving the pump 6 (S13) or deciding that the load is not above the upper limit $F_u$ (Ref. FIG. 11) (NO at S12), the control unit 7 decides whether the detected load is below the lower limit $F_b$ (Ref. FIG. 11) (S14). If the control unit 7 decides that the detected load is below the lower limit $F_b$ (Ref. FIG. 11) (YES at S14), the control unit 7 activates the pump 6 and then decides whether to finish the controlling operation of the pressure inside the cylindrical portion 12, i.e. for example whether the needle insertion has been completed (S16). The decision of the step S16 is also made when the control unit 7 has decided that the detected load is not below the lower limit $F_b$ (Ref. FIG. 11) (NO at S14).

If the control unit 7 decides not to finish the controlling operation of the pressure inside the cylindrical portion 12 (NO at S16), the control unit 7 repeats the steps S11 to S16. On the other hand, upon deciding to finish the controlling operation of the pressure inside the cylindrical portion 12 (YES at S16), the control unit 7 turns off the power for the pump 6 (S17).

The pressing force applied to the load sensor 54 by the movable body 50 has a close correlation with the swelling height of the skin Sk, which in turn is closely related with the pressure inside the cylindrical portion 12. Accordingly, the swelling height of the skin Sk can also be maintained within a certain range by controlling the operation of the pump 6 based on the output of the load sensor 54. Referring to FIG. 11, after activating the pump 6 at the time T1 and once the skin Sk has been sufficiently raised so as to cause the movable body 50 to press the load sensor 54 thus to turn it on at T2, solely controlling the negative pressure inside the cylindrical portion 12 can maintain the load detected by the load sensor 54 within the target load range delimited by the upper limit $F_u$ and the lower limit $F_b$, throughout the subsequent steps.

The lancing apparatus A2 according to this embodiment also allows achieving a generally constant swelling height of the skin Sk when inserting the needle, irrespective of the softness of the skin Sk, and thereby inserting the needle 21 of the lancet 2 by an appropriate depth into the skin Sk. Since a load sensor is relatively inexpensive in general, the system employing a load sensor is advantageous in reducing the cost of the lancing apparatus as a whole, yet allows properly performing the control to maintain the swelling height of the skin Sk at a generally constant level.

Figure 12:
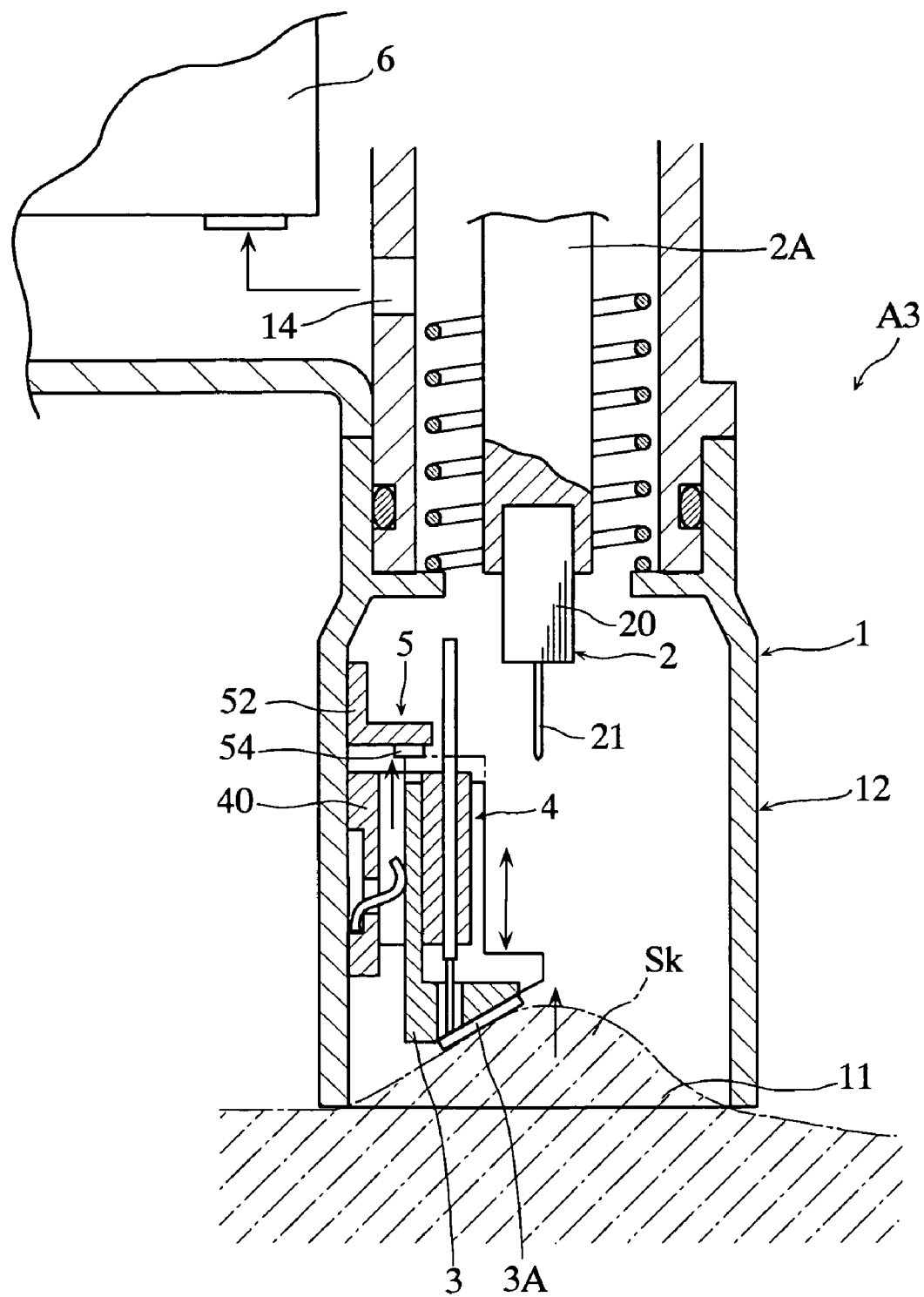
FIG. 12 is an enlarged fragmentary cross-sectional view showing a lancing apparatus according to a third embodiment of the present invention.

FIG. 12 illustrates a lancing apparatus according to a third embodiment. In the lancing apparatus A3, the detection switch 5 is located right above the attachment base 4, while the sensor holder 3 is vertically movable. Accordingly, in the lancing apparatus A3, the swelling motion of the skin Sk causes the sensor holder 3 to ascend thus to press the load sensor 54.

In the lancing apparatus A3, since the sensor holder 3 also serves to detect the swelling height of the skin Sk, the number of parts of the device can be reduced, which leads to reduction in manufacturing cost and in dimensions of the device.

Figure 13:
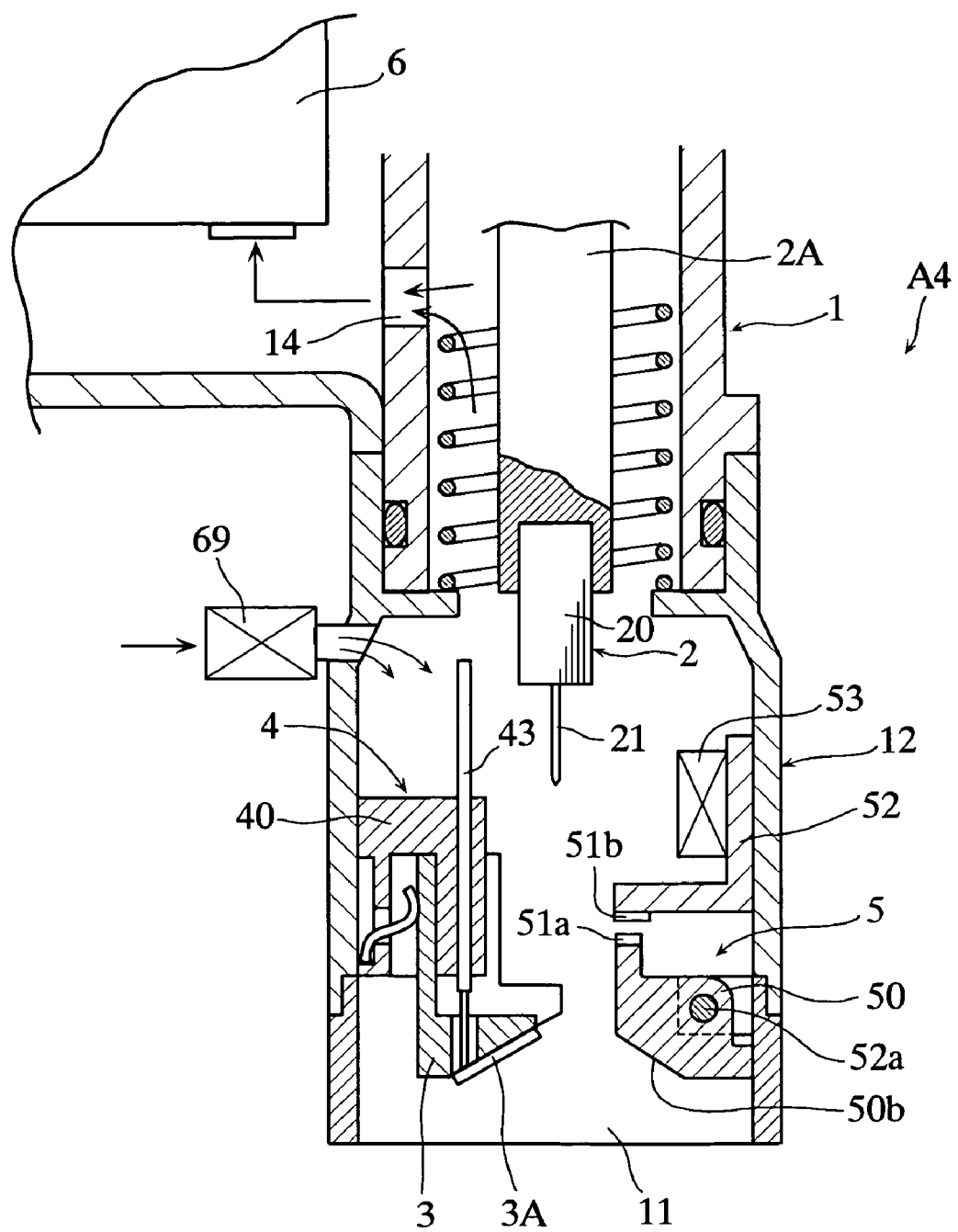
FIG. 13 is an enlarged fragmentary cross-sectional view showing a lancing apparatus according to a fourth embodiment of the present invention.

FIG. 13 illustrates a lancing apparatus according to a fourth embodiment. In the lancing apparatus A4, the housing 1 is provided with a relief valve 69. The relief valve 69 selects whether to allow communication between the inside and outside of the cylindrical portion 12, and is controlled to open or close by the control unit 7 (not shown in FIG. 13, but in FIG. 1).

In the lancing apparatus A4, while the pump 6 is constantly operating throughout the controlling process of the pressure inside the cylindrical portion 12, the relief valve 69 is closed when reducing the pressure inside the cylindrical portion 12, and is opened when increasing the pressure inside the cylindrical portion 12. This eliminates the need to perform the on/off control of the pump 6, and allows maintaining the pressure inside the cylindrical portion 12 within a target pressure range simply by opening and closing the relief valve 69.

Figure 14:
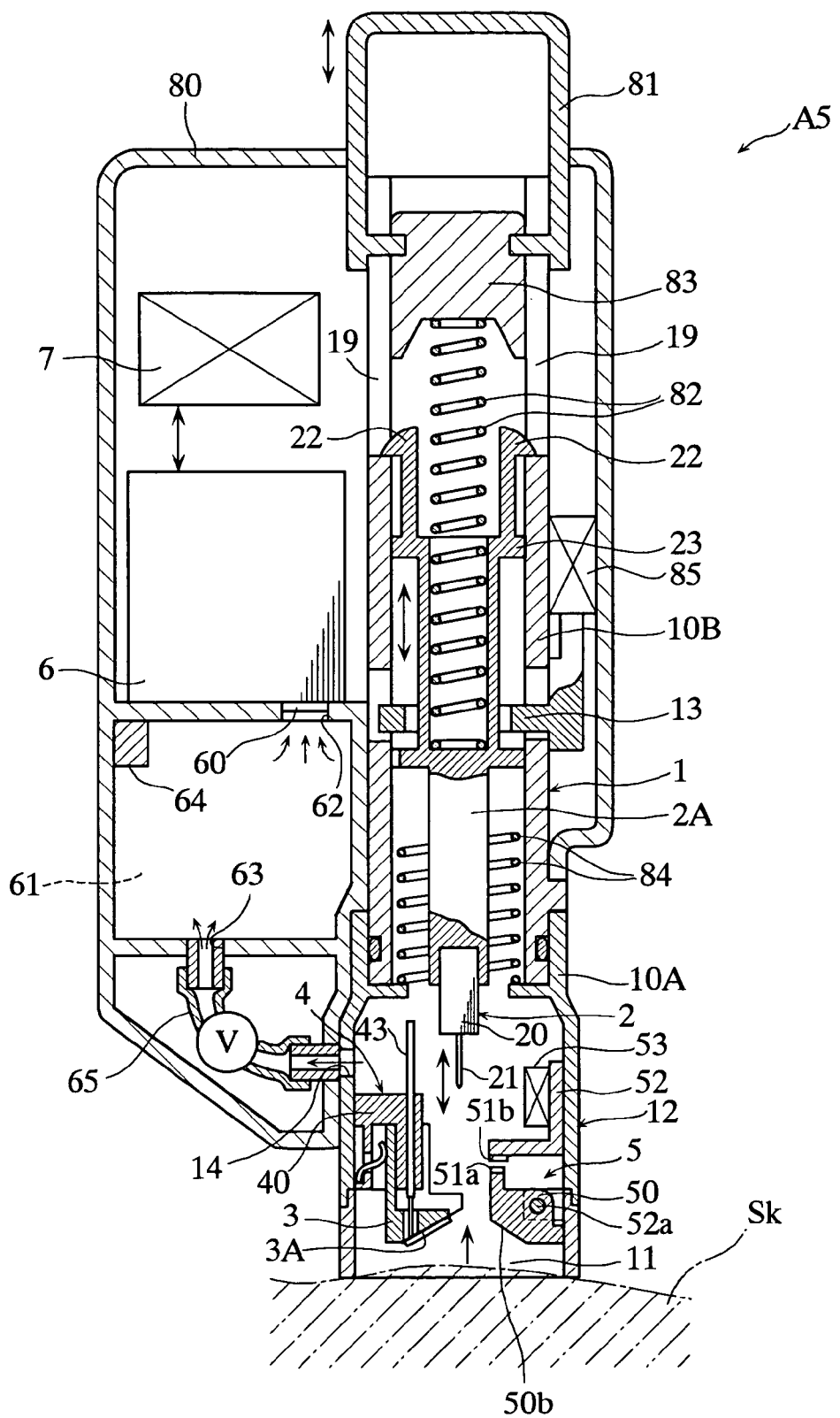
FIG. 14 is a cross-sectional view showing a lancing apparatus according to a fifth embodiment of the present invention.

FIG. 14 illustrates a lancing apparatus according to a fifth embodiment. The lancing apparatus A5 includes a backup chamber 61 for reducing the pressure inside the cylindrical portion 12 when it becomes higher than a target value (for example the second threshold value $P_2$ shown in FIG. 8).

The backup chamber 61 has an air outlet 62 and an air inlet 63, and accommodates therein a pressure sensor 64 for detecting the pressure in the backup chamber 61. The air outlet 62 is connected to the pump 6, so that the pump 6 can serve to discharge air out of the backup chamber 61. The air inlet 63 serves as a port through which the air inside the cylindrical portion 12 flows into the backup chamber 61, and is connected to the communication port 14 of the housing 1 via a tube 65. The tube 65 is provided with a valve V, which selects whether to allow communication between the inside of the cylindrical portion 12 and the backup chamber 61. The valve V is controlled to open and close by the control unit 7, according to the pressure inside the cylindrical portion 12, i.e. the pressure detected by the pressure sensor 53.

The pump 6, operated under control of the control unit 7, serves to discharge the air out of the backup chamber 61. In other words, the pump 6 is activated when raising the skin Sk, and when the pressure in the backup chamber 61 exceeds a predetermined value after raising the skin Sk.

By the lancing apparatus A5, the skin Sk is raised by generating a negative pressure inside the cylindrical portion 12 upon bringing the cylindrical portion 12 into close contact with the skin Sk. The negative pressure is generated upon activating the pump 6 with the valve V opened, and thus discharging the air out of the backup chamber 61 and the cylindrical portion 12. The backup chamber 61 interposed between the inside of the cylindrical portion 12 and the pump 6 can serve as a sound-shielding space when reducing the pressure inside the cylindrical portion 12. Accordingly, a noise from the working pump 6 can be kept from leaking outward.

The controlling process of the pressure inside the cylindrical portion 12 is basically similar to the flowchart according to FIG. 7. However, when the pressure inside the cylindrical portion 12 is higher than the second threshold value $P_2$, the valve V is opened so that the air inside the cylindrical portion 12 flows into the backup chamber 61, to thus reduce the pressure inside the cylindrical portion 12. On the other hand, when the pressure in the backup chamber 61 exceeds a predetermined value, the control unit 7 activates the pump 6 so as to reduce the pressure in the backup chamber 61 and to maintain the reduced level. Such arrangement allows maintaining an appropriate differential pressure between the backup chamber 61 and the inside of the cylindrical portion 12, and thereby creating a proper flow of air out of the cylindrical portion 12 into the backup chamber 61.

In the lancing apparatus A5, the pump 6 is not only exempted from constantly operating, but is only activated when the pressure in the cylindrical portion 12 and the backup chamber 61 both exceed a predetermined value. Accordingly, such a structure eliminates the need to constantly operate or frequently activate the pump 6. Therefore, the lancing apparatus A5 can suppress a noise or vibration originating from the pump operation, and thus reduce propagation of the vibration the skin Sk and hence the risk of improper positioning of the needle 21 for insertion. This prevents the blood that has come out of the skin Sk from splashing around, and reduces the pain of the needle that the user may feel. Further, since the operating time of the pump 6 can be shortened in the lancing apparatus A5, the energy consumption by the pump 6 can be reduced, and a pump of a relatively small output can be employed. Accordingly, in the case where a battery is used as the power source for the pump 6, the service life of the battery can be prolonged, and in the case of employing a smaller pump, the overall dimensions of the device can be reduced.

Figure 15:
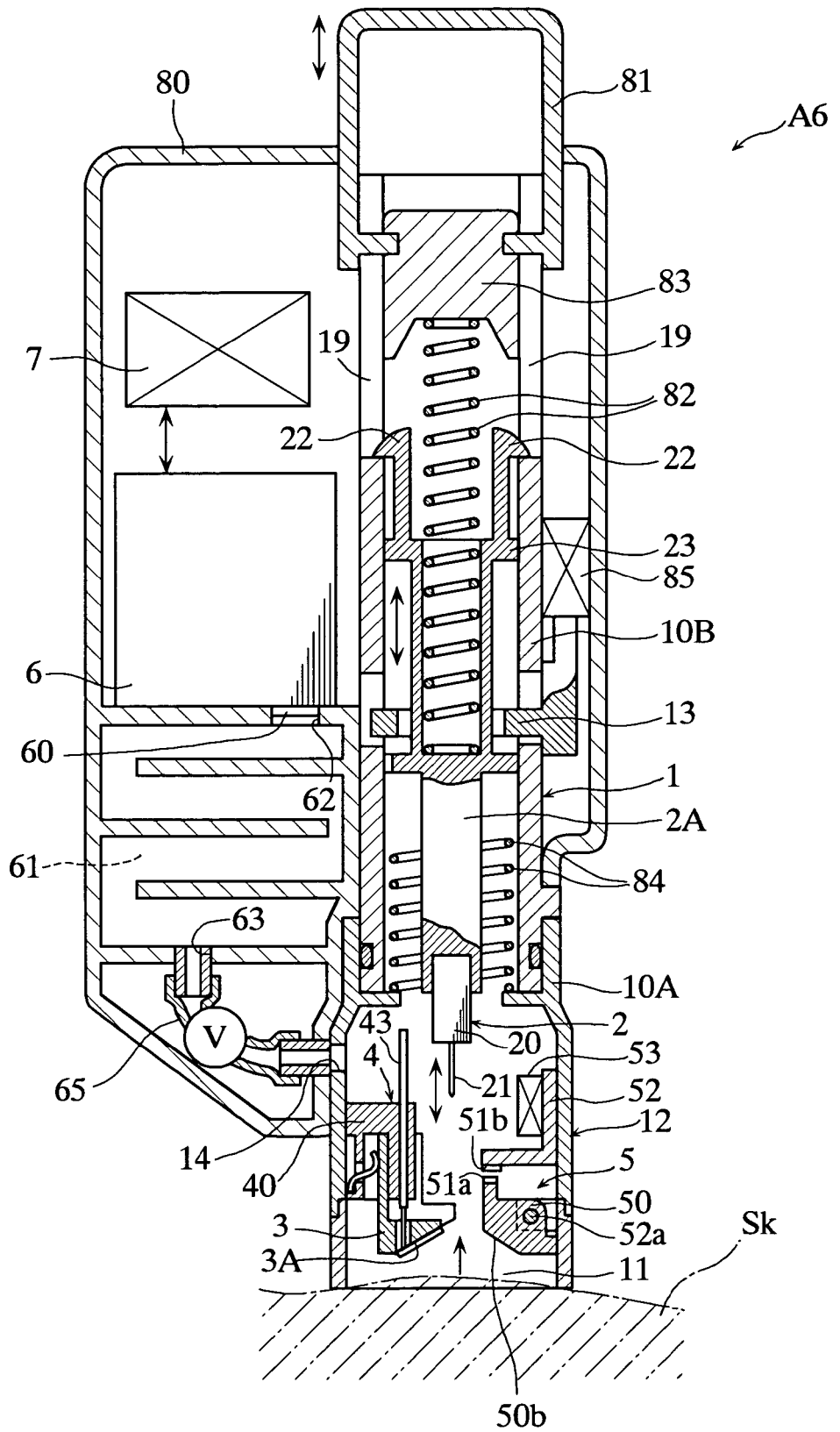
FIG. 15 is a cross-sectional view showing a lancing apparatus according to a sixth embodiment of the present invention.

FIG. 15 illustrates a lancing apparatus according to a sixth embodiment. In the lancing apparatus A6, the backup chamber 61 of the lancing apparatus A5 shown in FIG. 14 is converted into a flowing path. In other words, the backup chamber 61 serves as an extended flow path between the cylindrical portion 12 and the pump 6. A tube may be employed instead, to provide a backup chamber that performs a similar function.

Figure 16:
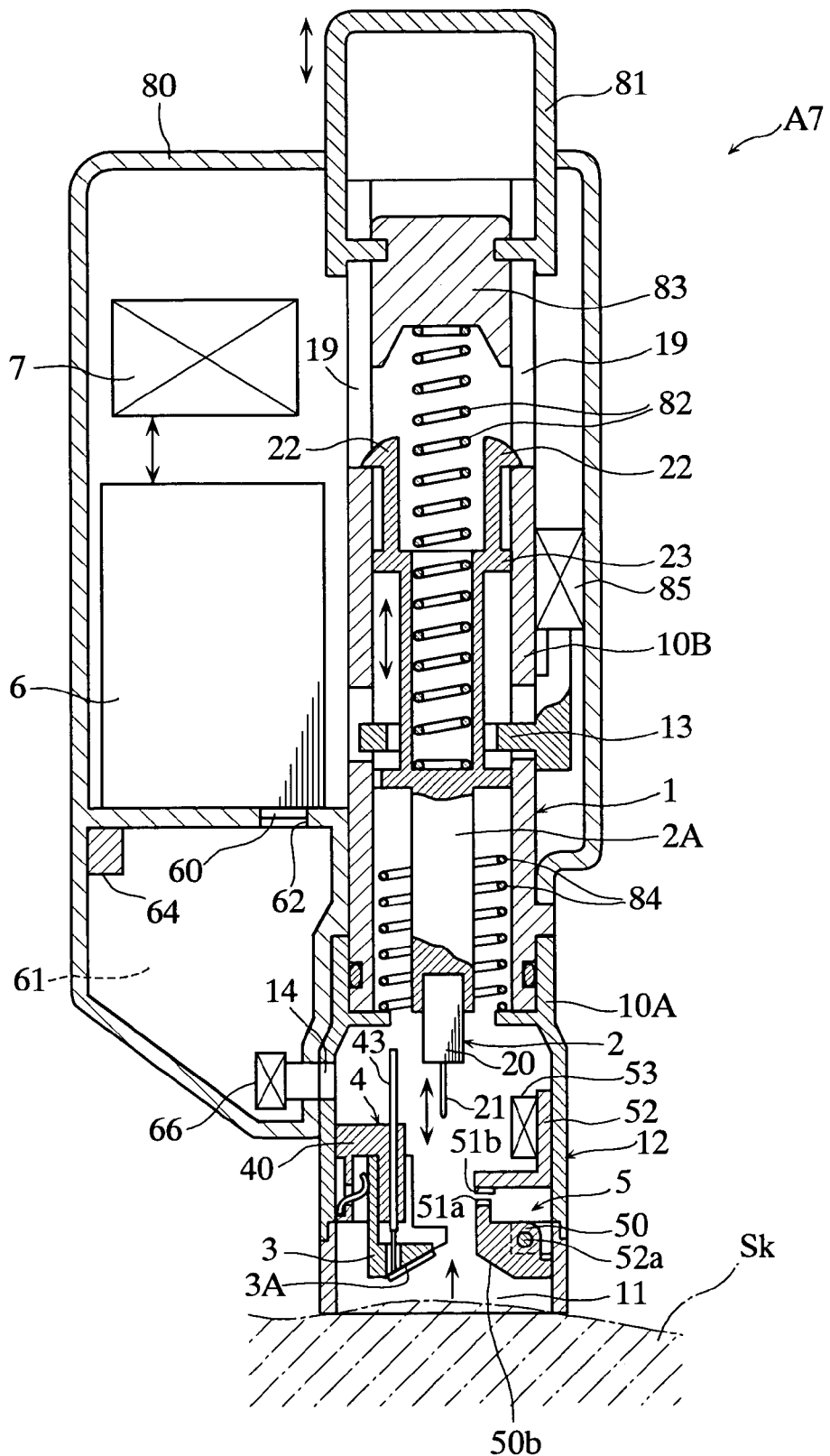
FIG. 16 is a cross-sectional view showing a lancing apparatus according to a seventh embodiment of the present invention.

FIG. 16 illustrates a lancing apparatus according to a seventh embodiment. In the lancing apparatus A7, a relief valve 66 is provided at the communication port 14 connecting the backup chamber 61 and the inside of the cylindrical portion 12. Accordingly, in the lancing apparatus A7, the relief valve 66 is replaced for the combination of the tube 65 and the valve V in the lancing apparatus A5 shown in FIG. 14.

The lancing apparatus A7 also allows, through the controlling the relief valve 66 by the control unit 7 in a similar manner to controlling the valve V (Ref. FIG. 14), maintaining the swelling height of the skin Sk within a certain range without constantly operating the pump 6, and irrespective of the stiffness of the skin Sk.

Figure 17:
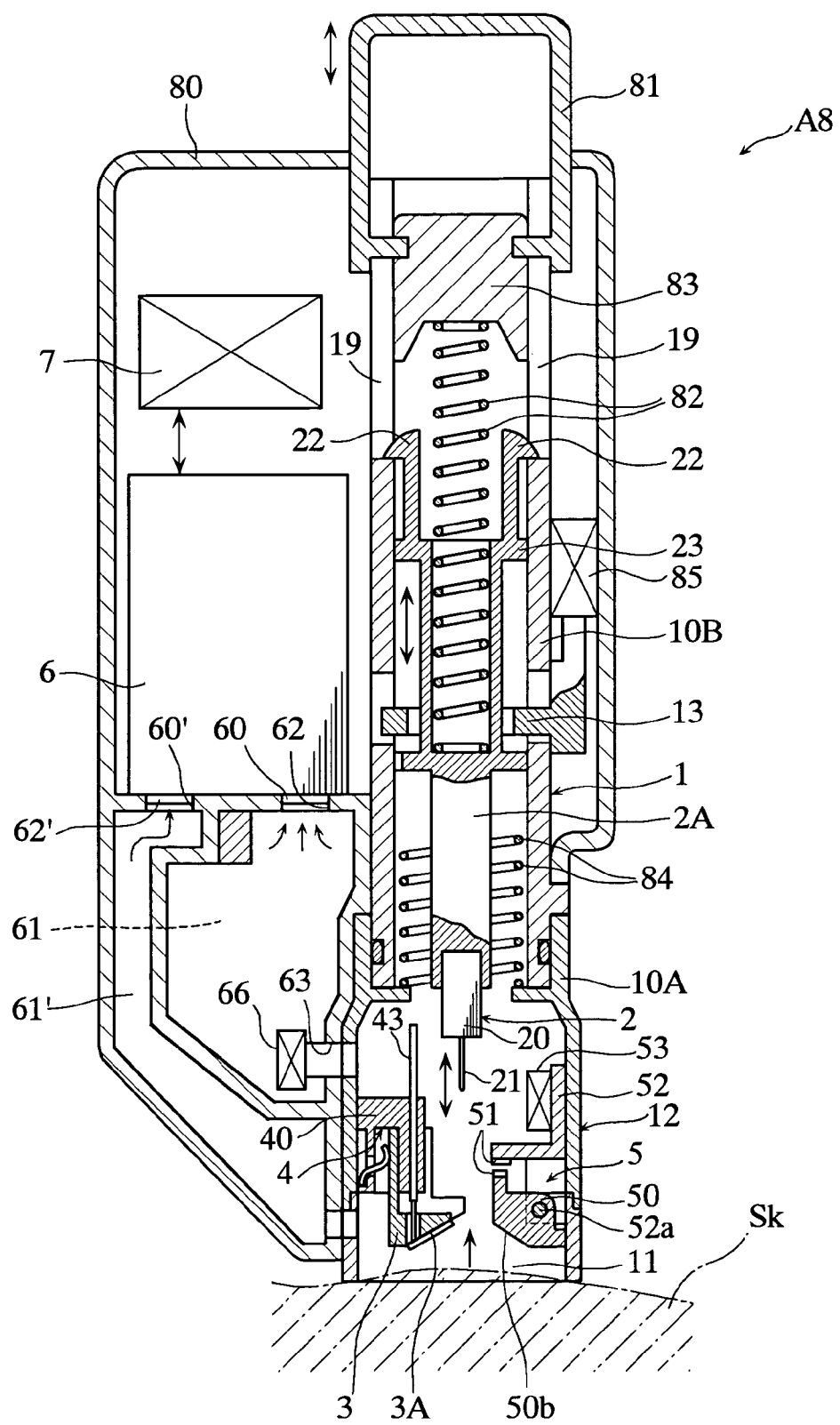
FIG. 17 is a cross-sectional view showing a lancing apparatus according to an eighth embodiment of the present invention.
Figure 18A:
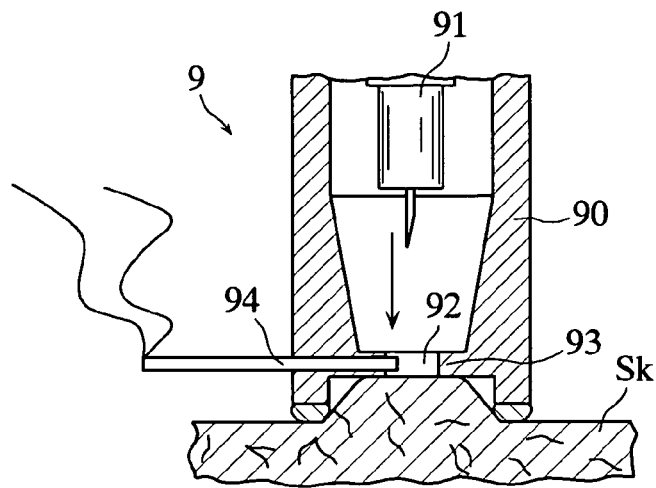
FIGS. 18A to 18C are fragmentary cross-sectional view of a conventional lancing apparatus.
Figure 18B:
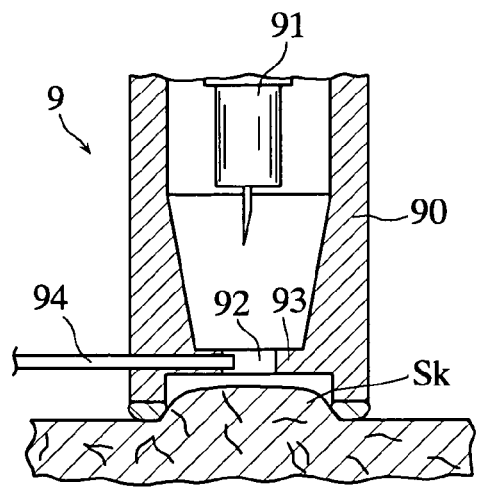
Figure 18C:
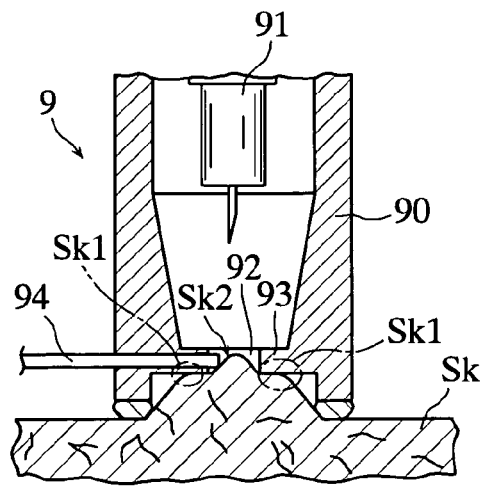

FIG. 17 illustrates a lancing apparatus according to an eighth embodiment. The lancing apparatus A8 allows independently performing the initial decompression control of the cylindrical portion 12, and the subsequent pressure control inside the cylindrical portion 12.

To be more detailed, the pump 6 and the inside of the cylindrical portion 12 are connected via the backup chamber 61 and a flow path 61'. In this structure the pump 6 is provided with two intake ports 60, 60', which are respectively communicating with the air outlet 62 of the backup chamber 61 and the air outlet 62' of the flow path 61'. At the air inlet 63 of the backup chamber 61, the relief valve 66 is provided.

It is to be understood that the present invention is not limited to the foregoing embodiments, but that the design of the components of the lancing apparatus according to the present invention may be modified in various manners.

To cite a few examples, the detector does not have to be a pressure sensor for detecting a pressure inside the cylindrical portion or a load sensor. The detector according to the present invention may be for example an optical sensor or a touch sensor, or alternatively a mechanical switch that is turned on when the skin is raised to a predetermined height.

In the present invention, the controlling operation to maintain a swelling height of the skin within a certain range may be omitted. For example, the lancet may be immediately caused to move forward once the sensor has detected that the skin has been raised to a predetermined height. Such a structure still allows constantly inserting the needle by an appropriate depth into the skin, and hence the object of the present invention can be achieved. When employing such a structure, it is preferable to employ a switch of a highly simplified mechanism.

The negative pressure generator according to the present invention is not limited to an electric pump. Although an electric pump provides various advantages such as simplicity in operation for a user, as well as in pressure control which can be performed simply by turning on and off the pump, a manual pump may be employed instead.

Further, for causing the lancet holder to move forward, an electromagnetic force or a pneumatic pressure may be employed, instead of utilizing a spring force.

Further, the analysis function for analyzing the blood extracted as a sample, or the attaching mechanism of the biosensor used for the sampling, may be omitted from the lancing apparatus according to the present invention.

The invention claimed is:

1. A lancing apparatus configured for sampling a body fluid out of a skin, the apparatus comprising a housing including a cylindrical portion adapted to be brought into contact with the skin, an insertion element movable relative to the housing for sticking the skin, and a negative pressure generator configured to generate a negative pressure inside the cylindrical portion to cause the skin to swell upward, wherein the apparatus further comprises a height detector and a pressure controller configured to cooperate with the height detector, the height detector being configured for detecting that the skin has been raised to a predetermined height inside the cylindrical portion, the height detector being provided separately from the insertion element and including a tapered face that is adapted to come into contact with the skin when the skin swells upward, the pressure controller being configured to execute a control so as to maintain a pressure inside the cylindrical portion within a specific range, the pressure controller being configured to execute the control based on detection by the height detector that the skin has been raised to the predetermined height, the pressure controller being configured to define the specific range by granting a specific tolerance to a reference pressure that the pressure controller is configured to set at a lower value than the pressure inside the cylindrical portion at a time that the height detector has detected that the skin has been raised to the predetermined height.

2. The lancing apparatus according to claim 1, further comprising a pressure detector that detects a pressure inside the cylindrical portion, wherein the controller is configured to execute a control so as to maintain a pressure inside the cylindrical portion within a specific range, based on the pressure detected by the pressure detector.

3. The lancing apparatus according to claim 1, wherein the specific range has an upper limit and a lower limit which the pressure controller is configured to set at a lower value than the pressure inside the cylindrical portion at the time that the height detector has detected that the skin has been raised to the predetermined height.

4. The lancing apparatus according to claim 1, wherein the height detector is capable of detecting a fluctuation of the swelling height of the skin, and wherein the controller is configured to control the pressure inside the cylindrical portion so as to maintain the swelling height of the skin at the predetermined level.

5. The lancing apparatus according to claim 4, wherein the height detector includes a contacting member for contact with the skin when the skin has been raised to the predetermined height, so as to detect a contacting pressure of the skin applied to the contacting member.

6. The lancing apparatus according to claim 5, wherein the controller is configured to control the pressure inside the cylindrical portion so as to maintain the contacting pressure within a set range.

7. The lancing apparatus according to claim 1, wherein the controller is configured to control the operation of the negative pressure generator so as to maintain a pressure inside the cylindrical portion within the specific range.

8. The lancing apparatus according to claim 1, further comprising a relief valve located at a position communicating with the inside of the cylindrical portion, wherein the controller is configured to control an opening and closing action of the relief valve so as to maintain the pressure inside the cylindrical portion within the specific range.

9. The lancing apparatus according to claim 8, wherein the controller is configured to open the relief valve when the pressure inside the cylindrical portion becomes equal or generally equal to a lower limit of the specific range.

10. The lancing apparatus according to claim 1, further comprising a backup chamber into which a gas inside the cylindrical portion flows when the pressure inside the cylindrical portion becomes equal or generally equal to an upper limit of the specific range, after generation of a negative pressure inside the cylindrical portion by the negative pressure generator.

11. The lancing apparatus according to claim 10, further comprising a gas supply selector controlled by the controller so as to select whether to supply a gas into the backup chamber.

12. The lancing apparatus according to claim 11, further comprising a cylindrical portion pressure detector that is configured to detect a pressure inside the cylindrical portion,
- wherein the gas supply selector comprises a relief valve that is configured to be opened or closed according to a detecting result given by the cylindrical portion pressure detector.

13. The lancing apparatus according to claim 10, wherein the backup chamber can be decompressed by the negative pressure generator.

14. The lancing apparatus according to claim 13, further comprising a backup chamber pressure detector that is configured to detect a pressure inside the backup chamber,
- wherein the negative pressure generator is configured to decompress the backup chamber when a pressure detected by the backup chamber pressure detector exceeds a predetermined threshold value.

15. The lancing apparatus according to claim 1, wherein the cylindrical portion includes an attachment base to which is removably attached a sampling element that is configured to sample a body fluid coming out of the skin by the insertion of the insertion element.

16. The lancing apparatus according to claim 1, wherein the cylindrical portion of the housing includes a plurality of members, and one or more of the members are removable from another.

17. The lancing apparatus according to claim 1, further comprising a controller that is configured to control an insertion depth into the skin or an inserting speed of the inserting element, based on a pressure inside the cylindrical portion at a time that the height detector has detected that the skin has been raised to the predetermined height.

18. The lancing apparatus according to claim 1, wherein the negative pressure generator comprises an electric pump.

19. The lancing apparatus according to claim 1,
- wherein the height detector comprises an optical sensor or a touch sensor.

20. The lancing apparatus according to claim 1, wherein the height detector is provided on a cylindrical internal surface of the cylindrical portion.

21. A lancing apparatus used for sampling a body fluid out of a skin, the apparatus comprising:
- a housing including a cylindrical portion that is adapted to be brought into contact with the skin;
- an insertion element movable relative to the housing for sticking the skin;
- a negative pressure generator that is configured to generate a negative pressure inside the cylindrical portion to cause the skin to swell upward;
- a height detector that is configured to detect that the skin has been raised to a predetermined height inside the cylindrical portion, the height detector being provided separately from the insertion element;
- a pressure detector that is configured to detect a pressure inside the cylindrical portion; and
- a controller that is configured to execute a control so as to maintain a pressure inside the cylindrical portion within a specific range, after the height detector has detected that the skin has been raised to the predetermined height, the controller being configured to define the specific range by granting a specific tolerance to a reference pressure;
- wherein the controller is configured to set the reference pressure based on the pressure detected by the pressure detector at a time that the height detector has detected that the skin has been raised to the predetermined height.

22. The lancing apparatus according to claim 21, wherein the setting of the reference pressure is performed whenever the sampling of the body fluid is performed.

23. The lancing apparatus according to claim 21, wherein the reference pressure is set at a lower value than the pressure detected by the pressure detector at the time that the height detector has detected that the skin has been raised to the predetermined height.

24. The lancing apparatus according to claim 21, wherein the specific range has an upper limit and a lower limit which are set at a lower value than the pressure detected by the pressure detector at the time that the height detector has detected that the skin has been raised to the predetermined height.

25. A blood sampling apparatus used for measuring glucose concentration in blood, the apparatus comprising:
- a housing including a cylindrical portion that is adapted to be brought into contact with skin;
- an insertion element movable relative to the housing for sticking the skin;
- a negative pressure generator for generating a negative pressure inside the cylindrical portion to cause the skin to swell upward;
- a height detector for detecting that the skin has been raised to a predetermined height inside the cylindrical portion; and
- a controller configured to cooperate with the height detector, the controller being configured to execute a control so as to maintain a pressure inside the cylindrical portion within a specific range, the controller being configured to execute the control based on detection by the height detector that the skin has been raised to the predetermined height;
- wherein the controller is configured to define the specific range by granting a specific tolerance to a reference pressure which the controller sets at a lower value than the pressure inside the cylindrical portion at a time that the height detector has detected that the skin has been raised to the predetermined height.

* * * * *